(12) United States Patent
Itotani et al.

(10) Patent No.: US 11,211,300 B2
(45) Date of Patent: Dec. 28, 2021

(54) ELECTRONIC COMPONENT AND CAMERA MODULE

(71) Applicant: SONY SEMICONDUCTOR SOLUTIONS CORPORATION, Kanagawa (JP)

(72) Inventors: Ryo Itotani, Kanagawa (JP); Yuta Momiuchi, Kanagawa (JP); Hirokazu Nakayama, Kanagawa (JP); Tooru Kai, Oita (JP); Miyoshi Togawa, Oita (JP)

(73) Assignee: SONY SEMICONDUCTOR SOLUTIONS CORPORATION, Kanagawa (JP)

( * ) Notice: Subject to any disclaimer, the term of this patent is extended or adjusted under 35 U.S.C. 154(b) by 187 days.

(21) Appl. No.: 16/471,853

(22) PCT Filed: Jan. 10, 2018

(86) PCT No.: PCT/JP2018/000334
§ 371 (c)(1),
(2) Date: Jun. 20, 2019

(87) PCT Pub. No.: WO2018/142856
PCT Pub. Date: Aug. 9, 2018

(65) Prior Publication Data
US 2020/0098691 A1    Mar. 26, 2020

(30) Foreign Application Priority Data

Jan. 31, 2017    (JP) .............................. JP2017-015842

(51) Int. Cl.
*H01L 23/28*    (2006.01)
*H01L 23/31*    (2006.01)
(Continued)

(52) U.S. Cl.
CPC ........ *H01L 23/3142* (2013.01); *H01L 21/563* (2013.01); *H01L 23/49811* (2013.01);
(Continued)

(58) Field of Classification Search
CPC ............... H01L 23/5381; H01L 21/563; H01L 23/49811; H01L 23/49894; H01L 24/17;
(Continued)

(56) References Cited

U.S. PATENT DOCUMENTS 5,920,126 A    7/1999  Sohara
6,153,930 A   11/2000  Hori
(Continued)

FOREIGN PATENT DOCUMENTS

JP    11-111894 A    4/1999
JP    11-214586 A    8/1999
(Continued)

OTHER PUBLICATIONS

International Search Report and Written Opinion of PCT Application No. PCT/JP2018/000334, dated Mar. 13, 2018, 11 pages of ISRWO.

*Primary Examiner* — Shouxiang Hu
(74) *Attorney, Agent, or Firm* — Chip Law Group

(57) ABSTRACT

To more securely hold reliability of an electronic component. There is provided an electronic component including a base material having a main face, at least one wiring formed on the main face of the base material, at least one pad provided at each end of the at least one wiring on the main face of the base material, a resist part formed to cover the at least one wiring on the main face of the base material, and a chip flip-chip mounted on the main face of the base material and connected to the base material via a bump bonded to the at least one pad, in which the resist part has a pad opening configured to expose the at least one pad
(Continued)

bonded with the bump, and a circulation groove formed to be connected to the pad opening at one end as a connection end to the pad opening.

15 Claims, 24 Drawing Sheets

(51) Int. Cl.
  *H01L 21/56* (2006.01)
  *H01L 23/498* (2006.01)
  *H01L 23/538* (2006.01)
  *H01L 23/00* (2006.01)

(52) U.S. Cl.
  CPC .... *H01L 23/49894* (2013.01); *H01L 23/5381* (2013.01); *H01L 23/562* (2013.01); *H01L 24/17* (2013.01); *H01L 2224/73204* (2013.01)

(58) Field of Classification Search
  CPC . H01L 2224/73204; H01L 2224/16237; H01L 27/14618; H01L 24/16; H01L 24/32; H01L 2224/26175; H01L 2224/92225; H01L 2224/83104; H01L 2224/81191; H01L 2224/13144; H01L 2924/19106; H01L 23/49838; H01L 23/12; H01L 2924/181; H01L 23/3142; H01L 23/562; H01L 23/3135
  See application file for complete search history.

(56) References Cited

U.S. PATENT DOCUMENTS

| | | | |
|---|---|---|---|
| 6,368,895 | B1 | 4/2002 | Hori |
| 6,518,656 | B1 | 2/2003 | Nakayama et al. |
| 6,566,745 | B1 * | 5/2003 | Beyne ............... H01L 27/14618 257/431 |
| 10,128,289 | B2 * | 11/2018 | Wu .................. H01L 27/14618 |
| 2006/0108656 | A1 * | 5/2006 | Minamio ............ H01L 31/0203 257/433 |
| 2014/0008679 | A1 | 1/2014 | Deguchi et al. |
| 2015/0001733 | A1 | 1/2015 | Karhade et al. |
| 2015/0228583 | A1 | 8/2015 | Karhade et al. |
| 2016/0300796 | A1 | 10/2016 | Karhade et al. |

FOREIGN PATENT DOCUMENTS

| | | |
|---|---|---|
| JP | 2001-119006 A | 4/2001 |
| JP | 2001-345391 A | 12/2001 |
| JP | 2004-349399 A | 12/2004 |
| JP | 2005-268567 A | 9/2005 |
| JP | 2005-327842 A | 11/2005 |
| JP | 2005-327842 A1 | 11/2005 |
| JP | 2013-232694 A | 11/2013 |
| KR | 10-2001-0040053 A | 5/2001 |
| WO | 2012/029318 A1 | 3/2012 |

* cited by examiner

ELECTRONIC COMPONENT AND CAMERA MODULE

CROSS REFERENCE TO RELATED APPLICATIONS

This application is a U.S. National Phase of International Patent Application No. PCT/JP2018/000334 filed on Jan. 10, 2018, which claims priority benefit of Japanese Patent Application No. JP 2017-015842 filed in the Japan Patent Office on Jan. 31, 2017. Each of the above-referenced applications is hereby incorporated herein by reference in its entirety.

TECHNICAL FIELD

The present disclosure relates to an electronic component and a camera module.

BACKGROUND ART

In recent years, an advanced process such as flip-chip mounting has been introduced into semiconductor chips such as image sensor mounted on a camera module realizing a shooting function of various shooting apparatuses, and chip shrink has increasingly advanced.

For example, Patent Document 1 described below discloses a technology for an electronic component having an imaging device flip-chip mounted on a circuit board.

CITATION LIST

Patent Document

Patent Document 1: Japanese Patent Application Laid-Open No. 2001-345391

SUMMARY OF THE INVENTION

Problems to be Solved by the Invention

Hardening encapsulation resin for sealing between a circuit board and a chip and fixing the circuit board and the chip is provided in the flip-chip mounted electronic component. However, the encapsulation resin may be hardened depending on a manufacture condition although it is not sufficiently filled between the circuit board and the chip. In this case, the encapsulation resin is hardened although it does not sufficiently flow around bumps electrically connecting the circuit board and the chip, and thus the bumps can corrode or a sufficient bonding strength of the bumps cannot be obtained.

Thus, the present disclosure proposes a novel and improved electronic component capable of more securely holding reliability of the electronic component, and a camera module.

Solutions to Problems

According to the present disclosure, there is provided an electronic component including a base material having a main face, at least one wiring formed on the main face of the base material, at least one pad provided at each end of the at least one wiring on the main face of the base material, a resist part formed to cover the at least one wiring on the main face of the base material, and a chip flip-chip mounted on the main face of the base material and connected to the base material via a bump bonded to the at least one pad, in which the resist part has a pad opening configured to expose the at least one pad bonded with the bump, and a circulation groove formed to be connected to the pad opening at one end as a connection end to the pad opening.

Further, according to the present disclosure, there is provided a camera module including a base material having a first face and a second face opposite to the first face, at least one wiring formed on the first face of the base material, at least one pad provided at each end of the at least one wiring on the first face of the base material, a resist part formed to cover the at least one wiring on the first face of the base material, a translucent member provided to oppose the second face of the base material and having optical transparency, an imaging device flip-chip mounted on the first face of the base material, having a light receiving face on a side opposing the translucent member, and connected to the base material via a bump bonded to the at least one pad, and a lens unit provided opposite to a side of the translucent member opposing the base material, in which the base material and the resist part have main openings where a region corresponding to the light receiving face is opened in plan view, respectively, and the resist part has a pad opening configured to expose the at least one pad bonded with the bump, and a circulation groove formed to connect to the pad opening at one end as a connection end to the pad opening.

Effects of the Invention

As described above, according to the present disclosure, it is possible to more securely hold reliability of the electronic component.

Additionally, the above effect is not necessarily restrictive, and any effect described in the present specification or other effect graspable from the present specification may be obtained together with the above effect or instead of the above effect.

MODE FOR CARRYING OUT THE INVENTION

Figure 1:
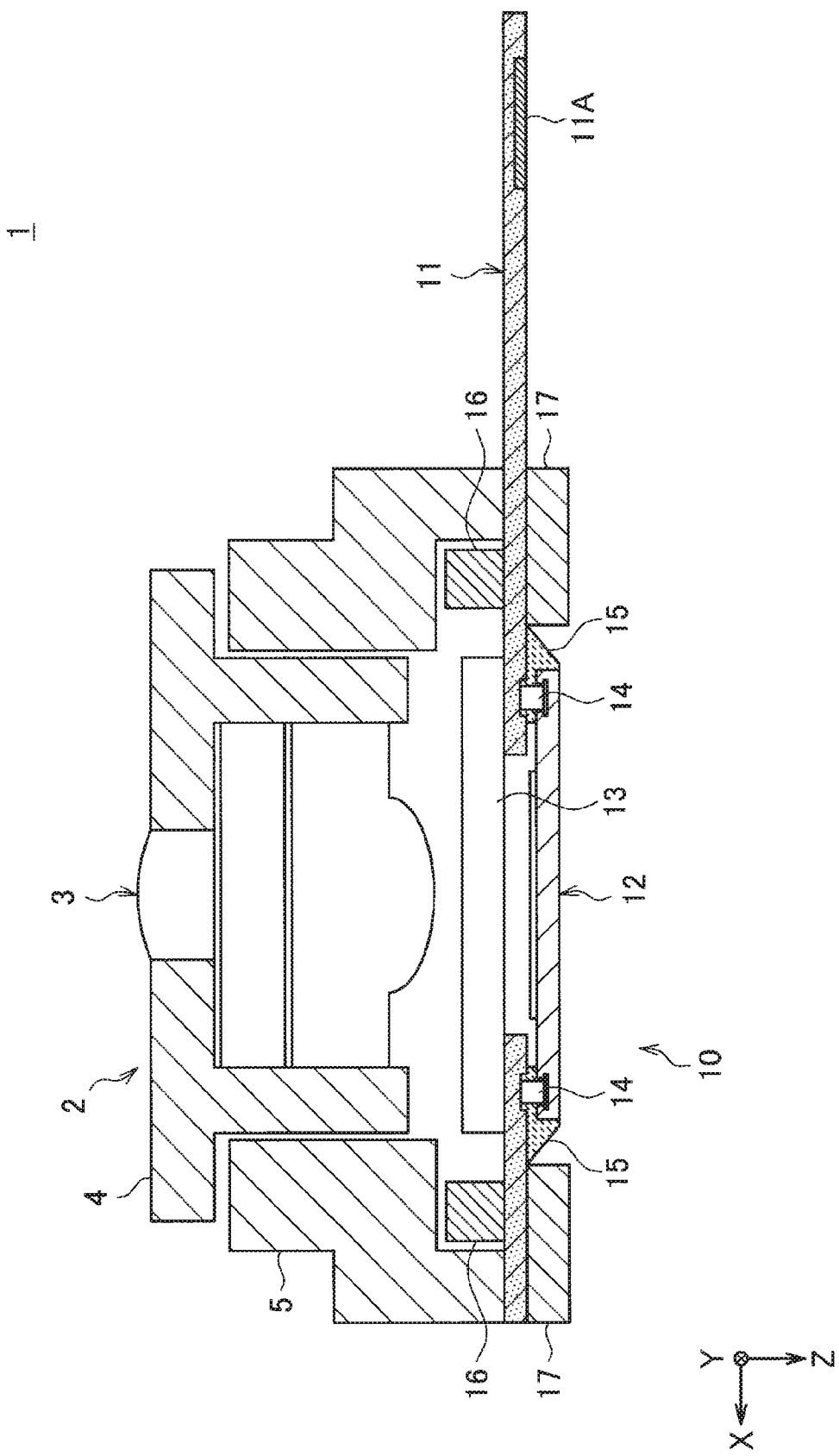
FIG. 1 is a cross-section view illustrating a schematic configuration of a camera module according to a first embodiment of the present disclosure.

Preferred embodiments of the present disclosure will be described below in detail with reference to the accompanying drawings. Additionally, the constituents having substantially the same functional configuration are denoted with the same reference numeral and a repeated description thereof will be omitted in the present specification and the drawings.

Further, the elements having substantially the same functional configuration may be discriminated by different alphabets after the same reference numeral in the present specification and the drawings. However, in a case where a plurality of elements having substantially the same functional configuration does not need to be particularly discriminated, only the same reference numeral is denoted.

Additionally, the description will be made in the following order.

1. Outline
2. First embodiment
2.1. Schematic configuration of camera module
2.2. Configuration of electronic component
2.3. Operations and effects
2.4. Variants
3. Second embodiment
3.1. Schematic configuration of camera module
3.2. Configuration of electronic component
3.3. Variant
4. Third embodiment
4.1. Schematic configuration of camera module
4.2. Configuration of electronic component
4.3. Variant
5. Application to in-vivo information acquisition system
6. Application to endoscopic surgery system
7. Application to moving object
8. Conclusion 1. Outline An electronic component according to a related technology will be described prior to describing an electronic component mounted on a camera module according to one embodiment of the present disclosure. Additionally, an electronic component in the present disclosure means an electronic component in which an imaging device as image sensor is flip-chip mounted on a circuit board, but the imaging device is an exemplary chip. That is, any kind of chip capable of being flip-chip mounted on a circuit board is possible, and the kinds of chip (such as large-scale integrated circuit (LSI) chip, for example) are not limited.

Figure 26:
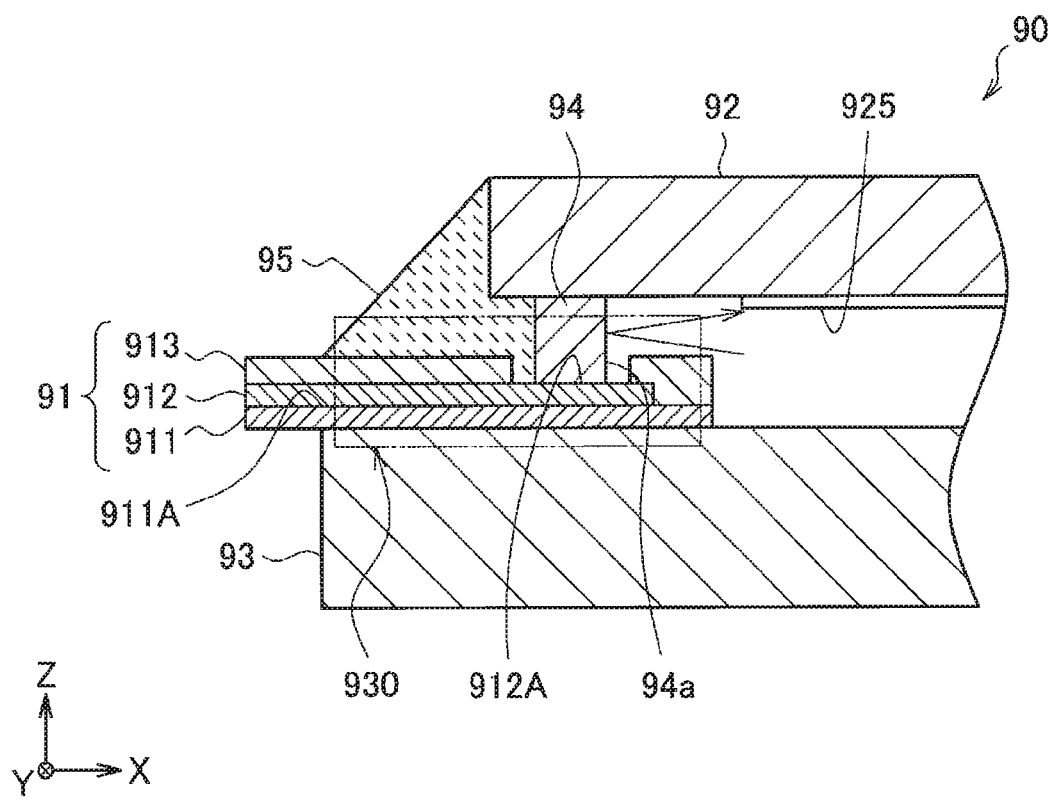
FIG. 26 is a cross-section view illustrating an exemplary configuration of an electronic component according to a related technology.

FIG. 26 is a cross-section view illustrating an exemplary configuration of an electronic component 90 according to a related technology. As illustrated in FIG. 26, the electronic component 90 includes a circuit board 91, an imaging device 92, a translucent member 93, bumps 94, and encapsulation resin 95.

The circuit board 91 is made of a base material such as polyimide, for example. As illustrated in FIG. 26, the circuit board 91 includes a base material 911, wiring 912, and a resist part 913. The wiring 912 are formed on a main face 911A of the base material 911 as illustrated in FIG. 26. The resist part 913 is formed to cover the wiring 912 on the main face 911A of the base material 911. Pads 920 are formed at the ends of the wiring 912. Further, a pad opening 913A is formed corresponding to the pads 920 on the resist part 913, and the pads 920 are exposed via the pad opening 913A.

The imaging device 92 is flip-chip mounted on the circuit board 91 via the bumps 94 formed at the terminals of the imaging device 92, and is electrically connected to the circuit board 91 via the pads. The imaging device 92 includes a light receiving face 925, and the light receiving face 925 opposes the translucent member 93. Further, the circuit board 91 and the imaging device 92 are fixed by the encapsulation resin 95 filled therebetween. The circuit board 91 and the imaging device 92 are sealed therebetween by the encapsulation resin 95. Additionally, the circuit board 91 and the translucent member 93 can be adhered to each other by adhesive resin or the like (not illustrated).

However, as illustrated in FIG. 26, the encapsulation resin 95 may be hardened depending on a manufacture condition in the electronic component 90 although it is not sufficiently filled between the circuit board 91 and the imaging device 92. In this case, the encapsulation resin may be hardened although it does not flow around the bumps 94 electrically connecting the circuit board 91 and the imaging device 92. Thereby, a sufficient bonding strength of the bumps 94 may not be obtained.

Figure 27:
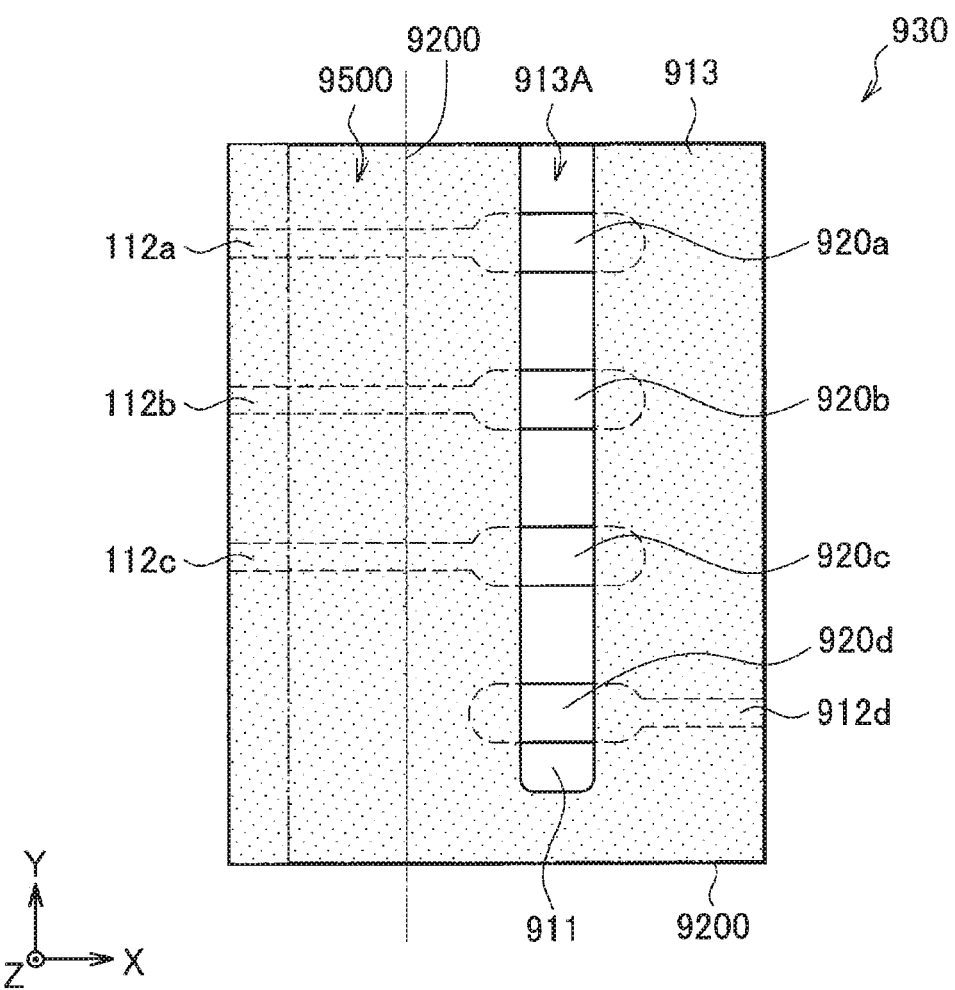
FIG. 27 is a top view of enlarged part of a circuit board according to the related technology.

FIG. 27 is a top view of enlarged part of the circuit board 91 according to the related technology. The top view is a diagram of the circuit board 91 included in a region 930 in FIG. 26 viewed from above.

As illustrated in FIG. 27, pads 920a to 920d are provided at the ends of four pieces of wiring 912a to 912d, respectively. Further, the pad opening 913A for exposing the top of the pads 920a to 920d is provided in the resist part 913. Further, the imaging device 92 is provided at a position where the bumps 94 oppose the pads 920 on the side of the main face 911A of the base material 911. A two-dot chain line 9200 indicates a peripheral end face when the imaging device 92 is flip-chip mounted. Further, the unhardened encapsulation resin 95 is applied in a region 9500.

The encapsulation resin 95 applied on the surface of the resist part 913 in the region 9500 flows in any direction in the electronic component 90. Thus, not all the encapsulation resin 95 flows into the pad opening 913A. Thus, the encapsulation resin 95 may not completely cover the side peripheral faces of the bumps 94 bonded to the pads 920. In this case, for example, the bumps 94 may corrode or a sufficient bonding strength between the pads 920 and the bumps 94 may not be secured. Thereby, a failure such as break can be caused at the bonding parts between the bumps 94 and the pads 920. In this case, reliability of the electronic component is difficult to hold.

Further, if the amount of encapsulation resin to be filled is increased or the encapsulation resin is hardened after being sufficiently filled, productivity in manufacturing the electronic component can lower.

Further, the encapsulation resin 95 may not sufficiently flow into the side peripheral faces 94a of the bumps 94 on an inner side of the electronic component 90. In a case where a chip configuring the electronic component 90 is the imaging device 92, light incident though the translucent member 93 reflects on the side peripheral faces 94a of the bumps 94 and its reflected light can enter the light receiving face 925. Thereby, a deterioration in image quality can be caused due to an occurrence of flare or ghost.

Therefore, a circulation groove for circulating encapsulation resin on the resist part of the circuit board toward the pad opening is formed in an electronic component according to one embodiment of the present disclosure. The configuration enables the encapsulation resin to easily circulate toward the pad opening. Thereby, the encapsulation resin is sufficiently filled around the bumps bonded to the pads (or the entire side peripheral faces).

Corrosion of the bumps can be prevented and the bonding strength between the pads and the bumps can be secured by the encapsulation resin hardened in this state, and thus reliability of the electronic component can be secured. Further, the encapsulation resin effectively flows toward the pad opening, and thus productivity of the electronic component can also be enhanced in terms of cost of materials and lead time. Further, if the encapsulation resin is sufficiently filled around the bumps, the intensity of reflected light from the side peripheral faces of the bumps is restricted, thereby preventing an occurrence of flare or ghost due to the reflected light.

An electronic component according to each embodiment of the present disclosure will be described below.

2. First Embodiment

A first embodiment of the present disclosure will be first described.

2.1. Schematic Configuration of Camera Module

FIG. 1 is a cross-section view illustrating a schematic configuration of a camera module 1 according to the first embodiment of the present disclosure. As illustrated in FIG. 1, the camera module 1 includes a lens unit 2, an electronic component 10, and a reinforcement plate 17. Additionally, the camera module 1 according to the present embodiment can be mounted on any apparatus having a shooting function, such as digital camera, Smartphone, cell phone, tablet, notebook-type personal computer (PC), home electronics, industrial devices, laboratory devices, transport machinery, or the like.

As illustrated in FIG. 1, the lens unit 2 includes a group of lenses 3, a holder 4 for fixing and supporting the group of lenses 3, and a housing 5 for supporting the holder 4 to be vertically movable. The above-described lens unit 2 is realized by a well-known lens unit. The lens unit 2 to be employed can be determined as needed depending on the specification of the imaging device 12 or the design items of the electronic component 10.

As illustrated in FIG. 1, the electronic component 10 includes a circuit board 11, an imaging device 12, a translucent member 13, bumps 14, encapsulation resin 15, and a passive component 16. A detailed configuration of the electronic component 10 except the passive component 16, and the functions of each constituent will be described below. An external terminal 11A capable of being electrically connected to other device can be formed on the lower face of the circuit board 11. The passive component 16 is a passive device realized by a chip capacitor, capacitor, or the like. The passive component 16 to be employed can be determined as needed by the design items of the electronic component 10.

Further, the reinforcement plate 17 can be provided for supporting the lens unit 2 and the electronic component 10. In the example illustrated in FIG. 1, the reinforcement plate 17 can be provided below the lower face of the circuit board 11 and at the lower part of the housing 5 in order to prevent the circuit board 11 from bending due to the weight of the lens unit 2.

2.2. Configuration of Electronic Component

Figure 2:
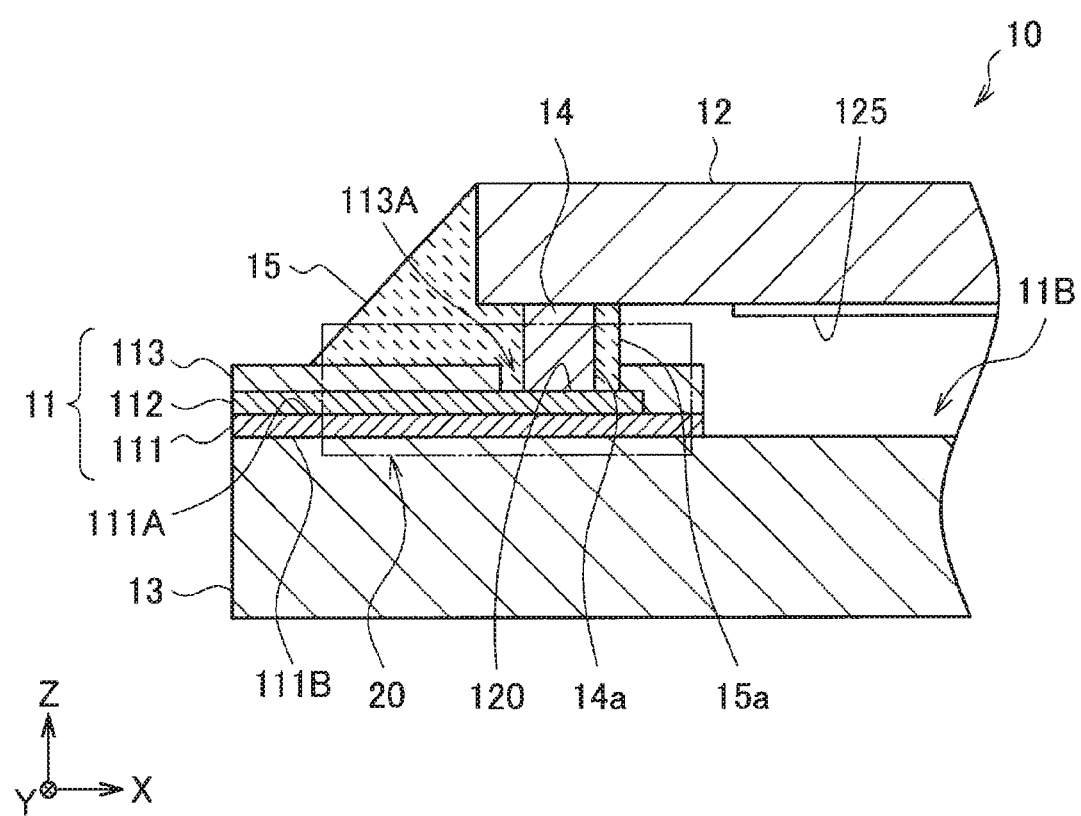
FIG. 2 is a cross-section view illustrating an exemplary configuration of an electronic component according to the embodiment.

An exemplary configuration of the electronic component 10 according to the present embodiment will be described below. FIG. 2 is a cross-section view illustrating an exemplary configuration of the electronic component 10 according to the present embodiment. The cross-section view illustrated in FIG. 2 is a diagram in which the bump 14 bonding the circuit board 11 and the imaging device 12 is mainly enlarged. Additionally, the configurations of the external terminal 11A and the passive component 16 are omitted from FIG. 2.

As illustrated in FIG. 2, the electronic component 10 includes the circuit board 11, the imaging device 12, the translucent member 13, the bumps 14, and the encapsulation resin 15.

The circuit board 11 can be a flexible board, a rigid flexible board, or the like made of a base material such as polyimide, for example. As illustrated in FIG. 2, the circuit board 11 includes a base material 111, wiring 112, and a resist part 113.

The wiring 112 is formed on a main face (corresponding to a first face) 111A of the base material 111 as illustrated in FIG. 2. The wiring 112 configures an electronic circuit on the circuit board 11. Further, pads 120 are formed at the ends of the wiring 112. The wiring 112 can be formed on the main face 111A of the base material 111 by use of a metal such as copper, for example.

The resist part 113 can be formed to cover the wiring 112 on the main face 111A of the base material 111. Further, a pad opening 113A is formed corresponding to the pads 120 in the resist part 113, and the pads 120 are exposed via the pad opening 113A. The resist part 113 can be made of a well-known resist member for manufacturing semiconductor chips, for example.

Further, the circuit board 11 includes a main opening 11B. Light collected by the group of lenses 3 in the lens unit 2 can pass through the main opening 11B and can enter the light receiving face 125 of the imaging device 12.

The imaging device 12 is an image sensor such as complementary metal oxide semiconductor (CMOS) image sensor, for example. The imaging device 12 has, for example, the light receiving face 125 in which unit pixels including photoelectric conversion devices (simply denoted as pixel below) are two-dimensionally arranged in a matrix shape, and senses the amount of charges depending on the amount of light incident into the light receiving face 125 as the physical amount in units of pixel.

The imaging device 12 is flip-chip mounted on the main face 111A of the base material 111. Here, the bumps 14 formed at the terminals of the imaging device 12 and the pads 120 are bonded so that the imaging device 12 is electrically connected to the circuit board 11.

The translucent member 13 is made of a translucent material such as glass or resin film, for example. The translucent member 13 may be an infrared ray cut filter (IRCF) made of glass, resin film, or the like having an infrared ray absorption function, for example, in order to restrict an occurrence of red color. Further, an IRCF as optical filter having an infrared ray absorption material may be adhered on the upper face or the lower face of the translucent member 13.

The translucent member 13 is provided to oppose the lower face 111B (corresponding to opposite face of the main face, or second face) of the base material 111. It is preferable that the translucent member 13 be as large as it can be positioned at least below the bumps 14 such that the bonding strength between the pads 120 and the bumps 14 is kept at a certain level or more. Further, the mutually-opposed faces of the circuit board 11 and the translucent member 13 can be adhered by adhesive resin (not illustrated).

The bumps 14 are protruded terminals formed on the terminals (not illustrated) of the imaging device 12. The bumps 14 are made of a metal such as gold, for example. When the imaging device 12 is flip-chip mounted on the circuit board 11, the bumps 14 can be bonded with the pads 120 on the circuit board 11. Thereby, the imaging device 12 is electrically connected to the circuit board 11.

The encapsulation resin 15 is thermosetting, photocurable, or photothermal curable resin, and is a member for sealing between the circuit board 11 and the imaging device 12. The encapsulation resin 15 is filled and hardened between the circuit board 11 and the imaging device 12 so that the circuit board 11 and the imaging device 12 are fixed to each other. The encapsulation resin 15 is filled in the gap between the circuit board 11 and the imaging device 12, and then is irradiated by light such as ultraviolet rays or heated to be hardened.

The encapsulation resin 15 according to the present embodiment flows into the side peripheral faces 14a of the bumps 14 inside the electronic component 10 as illustrated in FIG. 2 (encapsulation resin 15a). The encapsulation resin 15a is hardened between the circuit board 11 and the imaging device 12 to cover the side peripheral faces 14a of the bumps 14. Thereby, the bonding strength between the bumps 14 and the pads 120 is secured, and an occurrence of a failure such as break is prevented at the bonding parts between the bumps 14 and the pads 120. Thereby, high reliability of the electronic component 10 can be kept.

Figure 3:
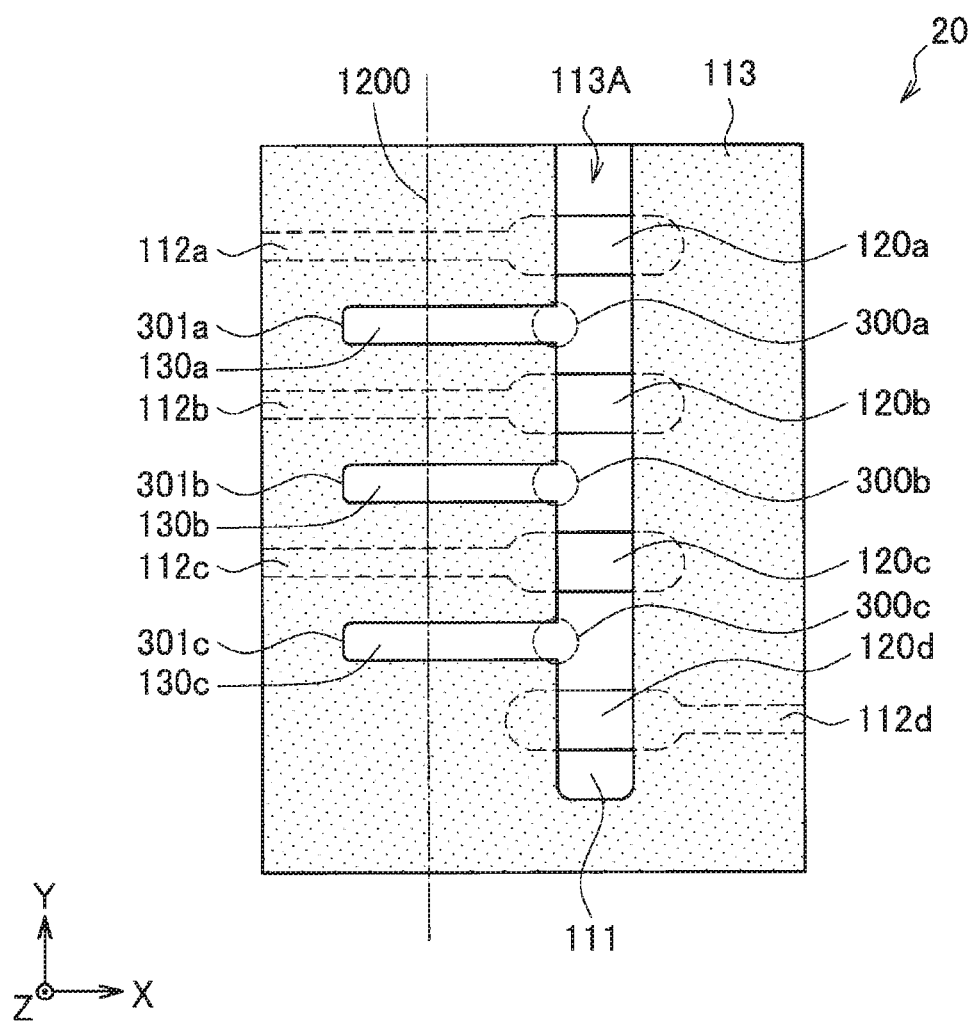
FIG. 3 is a top view of enlarged part of a circuit board according to the embodiment.

A configuration of the circuit board 11 for sufficiently circulating the encapsulation resin 15 around the side peripheral faces 14a of the bumps 14 will be described below with reference to FIG. 3. FIG. 3 is a top view of enlarged part of the circuit board 11 according to the present embodiment. The top view is a diagram of the circuit board 11 included in a region 20 in FIG. 2 viewed from above.

As illustrated in FIG. 3, the pads 120a to 120d are provided at the ends of the four pieces of wiring 112a to 112d, respectively. The pads 120a to 120d are arranged in a line on the main face 111A of the base material 111. Additionally, as many pads 120 illustrated in FIG. 3 as wiring 112 are provided. The number of pieces of wiring 112 to be arranged is set as needed depending on a design of the circuit. Further, the number of pads 120 to be arranged is set depending on the number of pieces of wiring 112 to be arranged.

The pad opening 113A for exposing the pads is provided above the pads 120a to 120d in the resist part 113. The pad opening 113A is formed in a groove shape to transversely expose the pads 120 in the region 20.

Further, the imaging device 12 is provided at a position where the bumps 14 oppose the pads 120 on the main face 111A of the base material 111. A two-dot chain line 1200 indicates a peripheral end face when the imaging device 12 is flip-chip mounted.

Then, the resist part 113 according to the present embodiment is provided with circulation grooves 130a to 130c connected to the pad opening 113A. The circulation grooves 130a to 130c are connected to the pad opening 113A at the ends (connection ends 300a to 300c) of the pad opening 113A side.

The circulation grooves 130 illustrated in FIG. 3 are provided to circulate the encapsulation resin 15 applied on the surface of the circuit board 11 toward the pad opening 113A. The circulation grooves 130 may be formed to extend in a direction orthogonal to a direction in which the groove-shaped pad opening 113A is formed as illustrated in FIG. 3. The circulation grooves 130 are formed in the direction so that the encapsulation resin 15 can be evenly filled toward the plurality of pads 120 (and the bumps 14 connected to the pads 120).

Additionally, the circulation grooves 130 may be formed such that the main face 111A of the base material 111 is exposed at the bottom of the circulation grooves 130. The circulation grooves 130 can be easily processed, and more encapsulation resin 15 can be flowed into the circulation grooves 130.

Further, the circulation grooves 130 can be formed in a region other than the region where the wiring 112 is formed on the main face 111A of the base material 111 as illustrated in FIG. 3. The circulation grooves 130 are formed around the wiring 112, thereby avoiding unintentional damage of the wiring 112.

Further, as illustrated in FIG. 3, the circulation grooves 130 may be formed such that the opposite ends 301 (301a to 301c) of the connection ends 300 of the circulation grooves 130 are to be outside the imaging device 12 in plan view in the resist part 113.

Packaging the electronic component 10 including the step of filling the encapsulation resin 15 will be described below with reference to FIG. 4 to FIG. 6.

Figure 4:
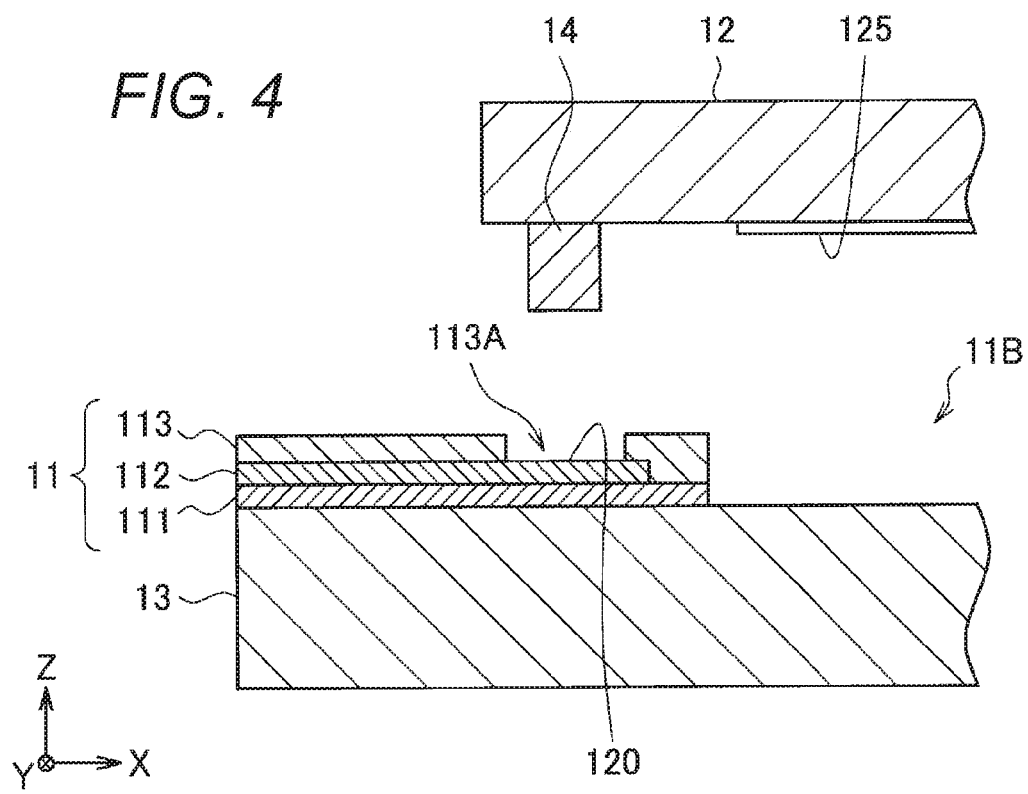
FIG. 4 is an outline diagram illustrating an exemplary step of packaging the electronic component according to the embodiment.
Figure 5:
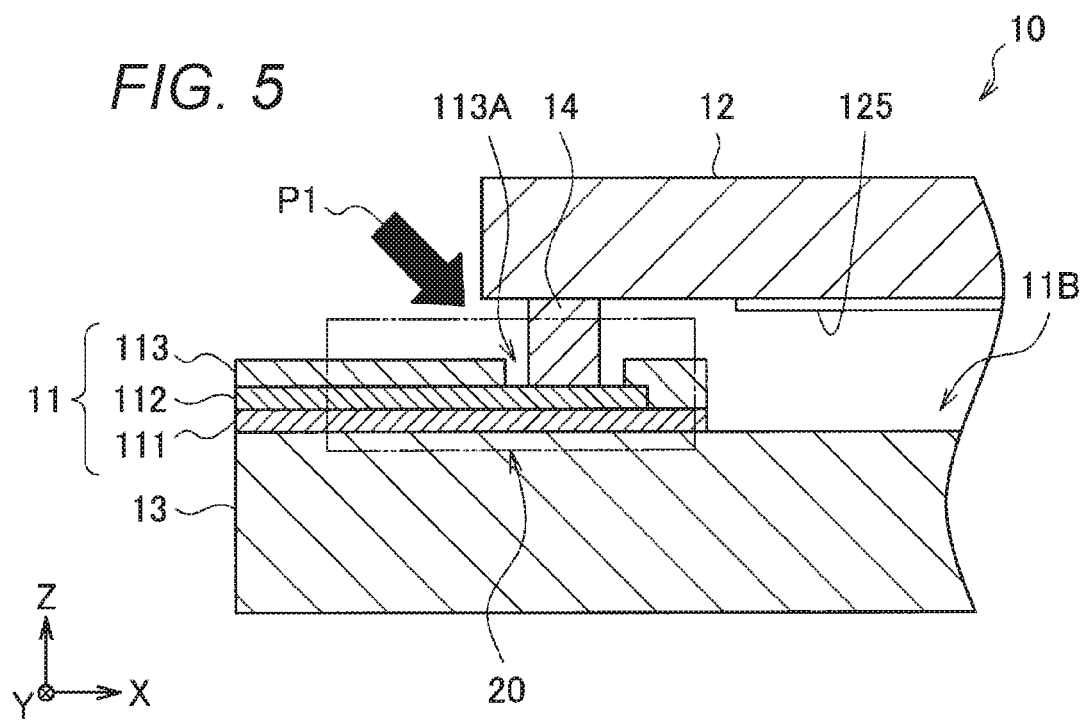
FIG. 5 is an outline diagram illustrating an exemplary step of packaging the electronic component according to the embodiment.

FIG. 4 and FIG. 5 are outline diagrams illustrating each exemplary step of packaging the electronic component 10 according to the present embodiment. At first, with reference to FIG. 4, the imaging device 12 with the bumps 14 formed is flip-chip mounted on the circuit board 11 bonded with the translucent member 13. At this time, the circuit board 11 and the imaging device 12 are combined such that the bumps 14 contact with the pads 120 at the wiring 112. Then, the bumps 14 and the pads 120 are contacted, and then the bumps 14 and the pads 120 are bonded in a well-known bonding method (see FIG. 5).

Next, with reference to FIG. 5, the encapsulation resin 15 is filled between the circuit board 11 and the imaging device 12 (in a space indicated by the arrow P1). The encapsulation resin 15 is filled and then hardened so that the space between the circuit board 11 and the imaging device 12 is sealed and the circuit board 11 and the imaging device 12 are fixed.

2.3. Operations and Effects

Figure 6:
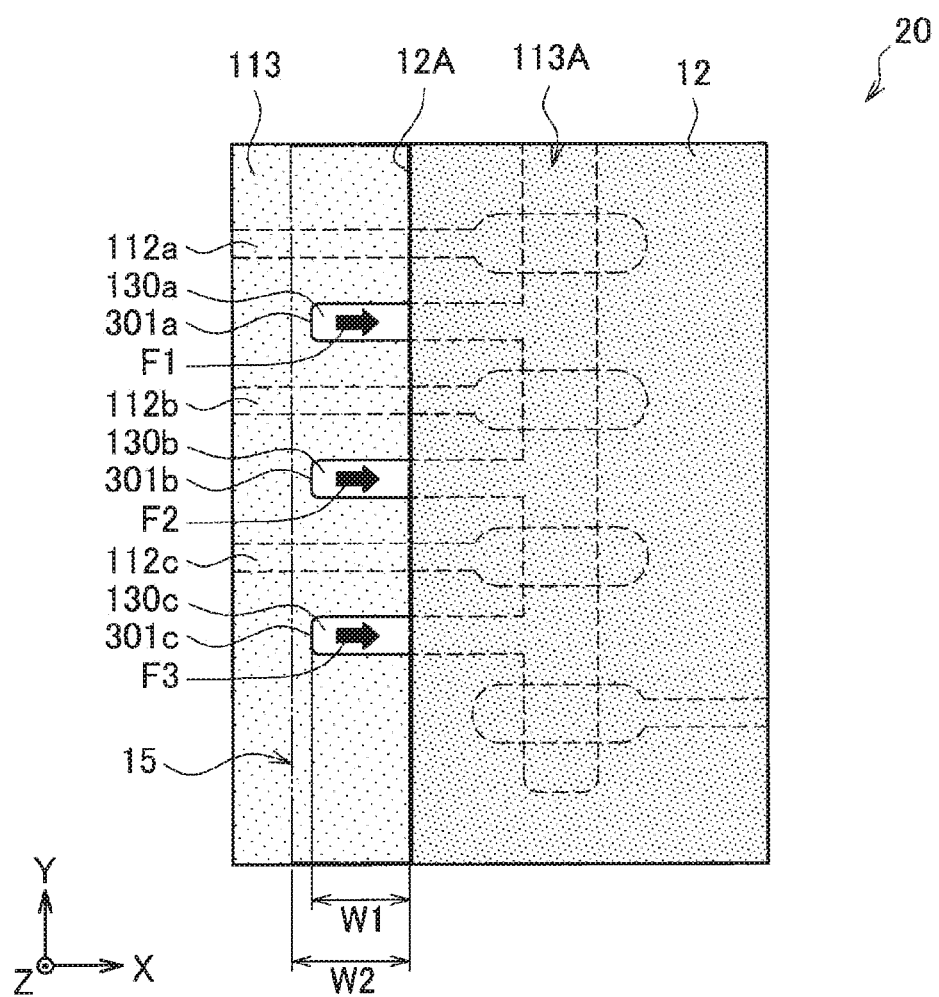
FIG. 6 is a top view of enlarged part of the electronic component according to the embodiment.

FIG. 6 is a top view of enlarged part of the electronic component 10 according to the present embodiment. The top view is a diagram of the electronic component 10 included in the region 20 in FIG. 5 viewed from above.

As illustrated in FIG. 6, part of the encapsulation resin 15 filled between the circuit board 11 and the imaging device 12 flows into the circulation grooves 130. The encapsulation resin 15 flowed into the circulation grooves 130 can flow in the direction in which the circulation grooves 130 are formed. Thus, the encapsulation resin 15 flowed into the circulation grooves 130 is determined in its flowing direction, and more easily flows toward the pad opening 113A than the encapsulation resin 15 not flowed into the circulation grooves 130. Thereby, the encapsulation resin 15 easily flows around the side peripheral faces 14a of the bumps 14.

Thus, the encapsulation resin 15a covering the side peripheral faces 14a of the bumps 14 can be formed as illustrated in FIG. 2. Therefore, corrosion of the bumps 14 can be prevented and the bonding strength of the bumps 14 can be kept higher, thereby securing reliability of the electronic component 10. Further, the encapsulation resin 15 efficiently flows into the pad opening 113A via the circulation grooves 130 so that the side peripheral faces 14a of the bumps 14 can be covered with a small amount of encapsulation resin 15 in a short time. Thereby, productivity of the electronic component 10 can be enhanced.

Further, the entire side peripheral faces 14a of the bumps 14 are covered with the encapsulation resin 15a, thereby reducing reflected light which can enter the light receiving face 125 of the imaging device 12 from the side peripheral faces 14a of the bumps 14. Thereby, an occurrence of flare or ghost due to reflected light can be restricted, thereby preventing a reduction in image quality.

Additionally, the encapsulation resin 15 may be made of absorbent resin. The resin may contain a black material such as carbon material, for example. Thereby, reflected light can be further reduced. Further, stray light, which can invade inside the electronic component 10 from the outer surface of the encapsulation resin 15, can be reduced.

Further, when the encapsulation resin 15 is filled, the encapsulation resin 15 may be applied on the surface of the circuit board 11 outside the gap between the circuit board 11 and the imaging device 12 as illustrated in FIG. 6. As illustrated in FIG. 6, the ends 301 of the circulation grooves 130 are positioned outside a peripheral end 12A of the imaging device 12 in plan view so that the encapsulation resin 15 leaked outside from the gap between the circuit board 11 and the imaging device 12 easily flows into the circulation grooves 130. Thereby, more encapsulation resin 15 can flow into the pad opening 113A.

Additionally, it is preferable that a length W1 from the peripheral end 12A of the imaging device 12 to the ends 301 in the circulation grooves 130 in plan view be equal to or less than a fillet width W2 as a length by which the encapsulation resin 15 leaks outside from the peripheral end 12A of the imaging device 12. That is, it is preferable that the ends 301 of the circulation grooves 130 be positioned in a region at the fillet width W2 or less from the peripheral end 12A of the imaging device 12. Thereby, the encapsulation resin 15 is filled also in the circulation grooves 130, thereby preventing foreign materials from mixing into the circulation grooves 130.

2.4. Variants

Variants of the present embodiment will be described below.

First Variant

Figure 7:
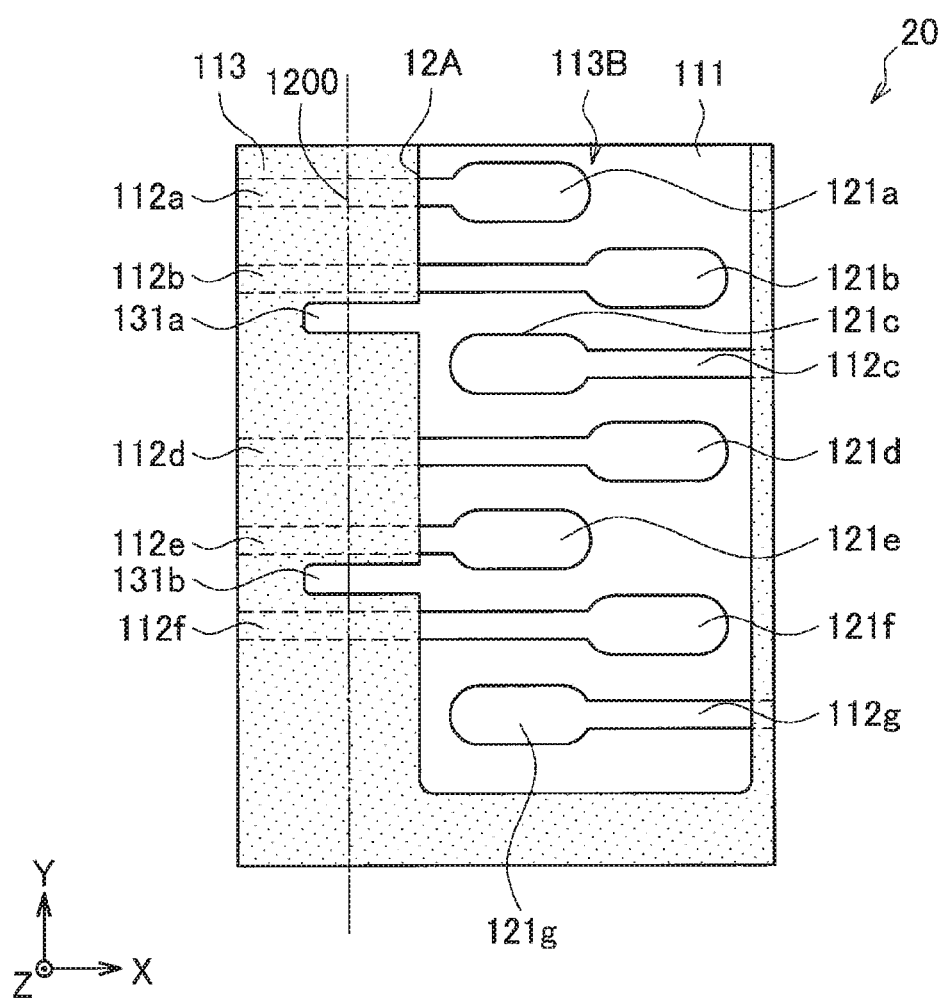
FIG. 7 is a top view of enlarged part of the circuit board according to a first variant of the embodiment.

FIG. 7 is a top view of enlarged part of the circuit board 11 according to a first variant of the present embodiment. The top view corresponds to a diagram of the circuit board 11 included in the region 20 in FIG. 2 viewed from above.

Pieces of wiring 112a to 112g are formed on the main face 111A of the base material 111 and pads 121a to 121g are formed at the ends of the wiring 112a to 112g, respectively, in the region 20 of the circuit board 11 illustrated in FIG. 7. The pads 121a to 121g are formed in a plurality of lines. In the example illustrated in FIG. 7, the pads 121a to 121g are formed in parallel in a houndstooth check manner. Further, the imaging device 12 is provided at a position where the bumps 14 oppose the pads 120 on the main face 111A of the base material 111. The two-dot chain line 1200 indicates a peripheral end face when the imaging device 12 is flip-chip mounted.

Further, a groove-shaped pad opening 113B for transversely exposing the pads 121a to 121g is formed on the resist part 113 formed above the main face 111A of the base material 111. Then, circulation grooves 131a and 131b are formed in a direction orthogonal to the direction in which the groove-shaped pad opening 113B is formed, and are connected to the pad opening 113B.

Also with the configuration, when the imaging device 12 is flip-chip mounted on the circuit board 11 and the encapsulation resin 15 is filled therebetween, the encapsulation resin 15 flows along the circulation grooves 131 and easily flows around the bumps 14 bonded to the pads 121. Thereby, even in a case where the pads 121 are formed in a plurality of lines, the encapsulation resin 15 can be securely filled in the pads 121.

Additionally, the pad opening formed to expose the pads is not limited to groove-shaped ones as illustrated in FIG. 3 and FIG. 7. As long as the pad opening is formed on the resist part to expose the pads, a form in which the pad opening is formed is not particularly limited. For example, one pad opening may be independently formed for each pad.

Further, the circulation grooves do not need to be formed for all the pad openings. The circulation grooves have only to be connected to the pad openings formed for the pads bonded with the bumps. Further, a direction in which the circulation grooves are formed for the pad opening is not particularly limited.

Second Variant

Figure 8:
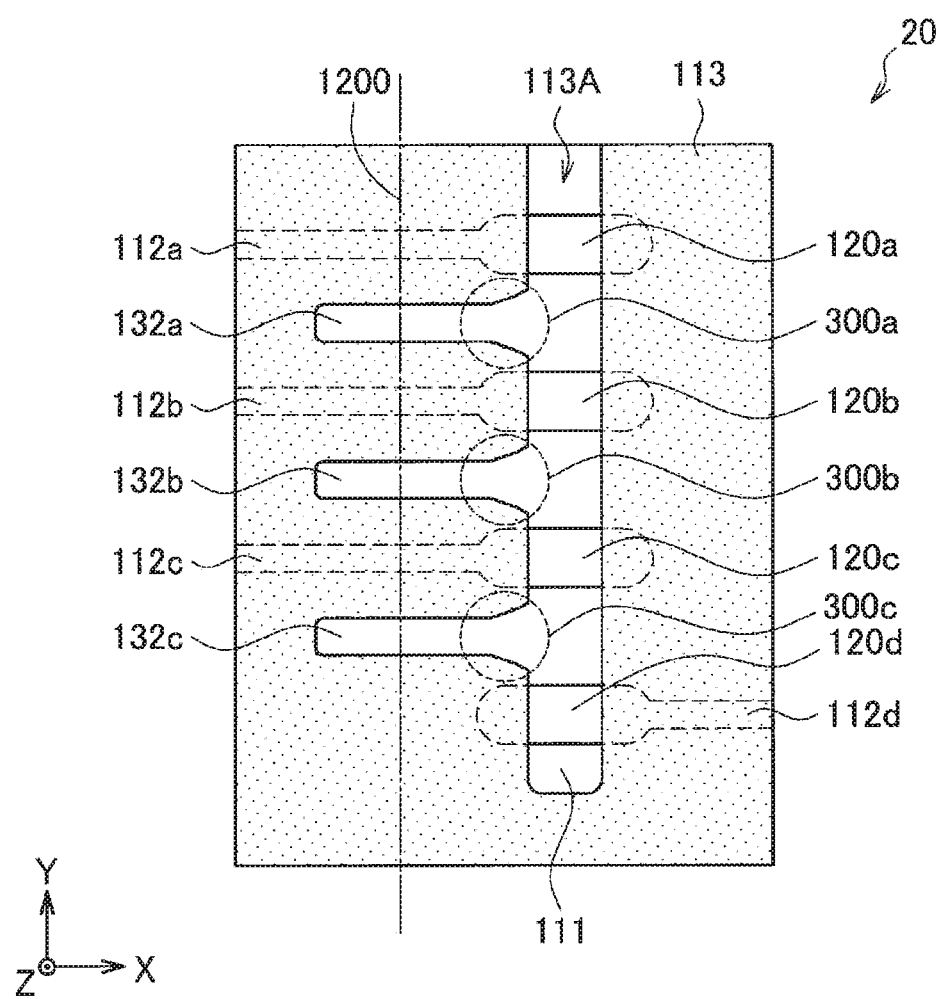
FIG. 8 is a top view of enlarged part of the circuit board according to a second variant of the embodiment.

FIG. 8 is a top view of enlarged part of the circuit board 11 according to a second variant of the present embodiment. The top view is a diagram of the circuit board 11 included in the region 20 in FIG. 2 viewed from above.

The pieces of wiring 112a to 112d are formed on the main face 111A of the base material 111 and the pads 120a to 120d are formed at the ends of the pieces of wiring 112a to 112d, respectively, in the region 20 of the circuit board 11 illustrated in FIG. 8. Further, the groove-shaped pad opening 113B for transversely exposing the pads 120a to 120d is formed on the resist part 113 formed above the main face 111A of the base material 111. Then, circulation grooves 132a to 132c are formed in a direction orthogonal to the direction in which the groove-shaped pad opening 113A is formed, and are connected to the pad opening 113A. Specifically, the circulation grooves 132a to 132c are connected to the pad opening 113A at the ends (connection ends 300a to 300c) of the pad opening 113A. Further, the imaging device 12 is provided at a position where the bumps 14 oppose the pads 120 on the main face 111A of the base material 111. The two-dot chain line 1200 indicates a peripheral end face when the imaging device 12 is flip-chip mounted.

The circulation grooves 132 according to the present variant are formed such that the groove width of the circulation groove 132 at the connection end 300 is larger than the groove width of the circulation groove 132 at a part other than the connection end 300. In the example illustrated in FIG. 8, the circulation grooves 132 are formed such that the groove width is larger from the circulation groove 132 toward the pad opening 113A near the connection end 300 of the circulation groove 132.

With the configuration, the encapsulation resin 15 flowing into the circulation grooves 132 and then flowing toward the pad opening 113A is easily dispersed in the pad opening 113A. Thereby, the encapsulation resin 15 is widely dispersed in the pad opening 113A and more easily flows around the bumps 14 bonded to the pads 120.

Third Variant

Figure 9:
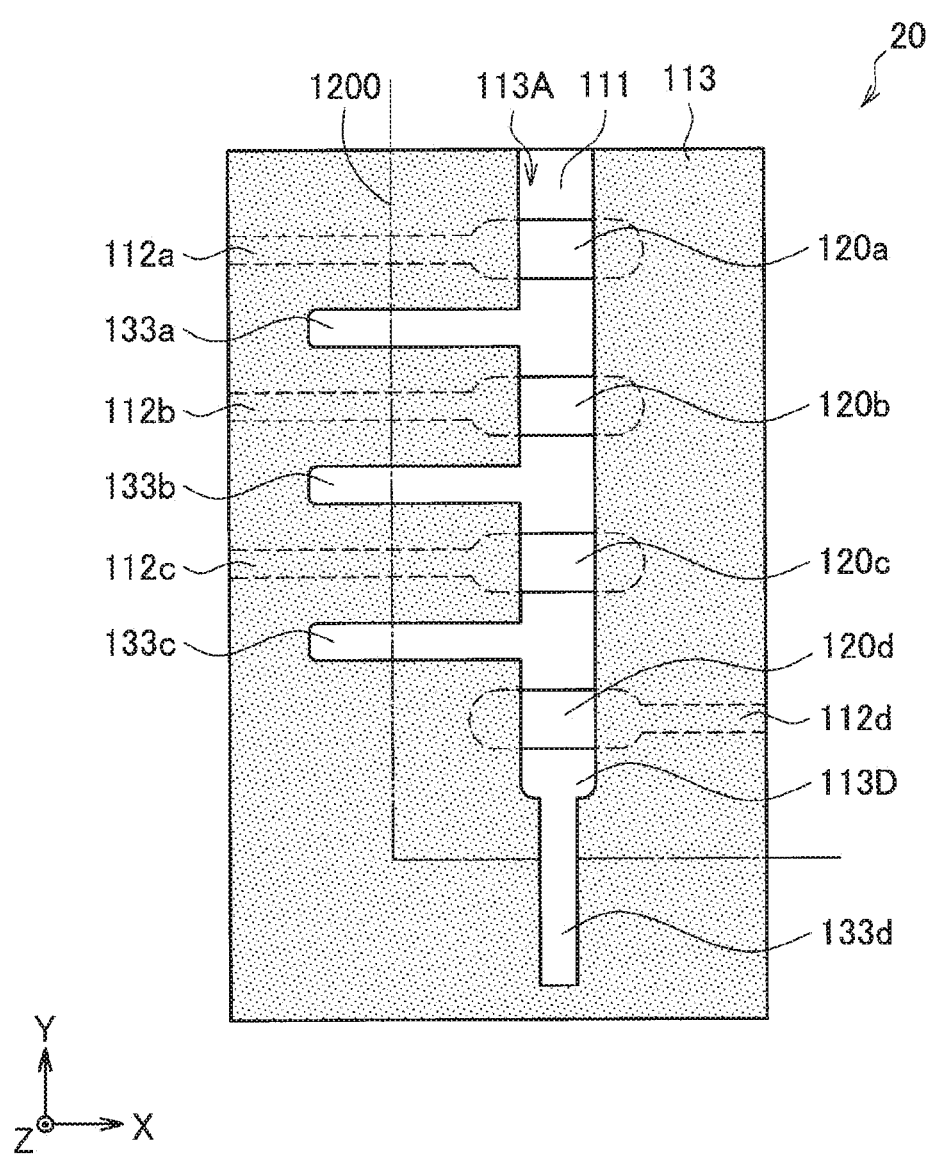
FIG. 9 is a top view of enlarged part of the circuit board according to a third variant of the embodiment.

FIG. 9 is a top view of enlarged part of the circuit board 11 according to a third variant of the present embodiment. The top view corresponds to a diagram of the circuit board 11 included in the region 20 in FIG. 2 and in the region corresponding to the corners of the imaging device 12 viewed from above.

The pieces of wiring 112a to 112d are formed on the main face 111A of the base material 111 and the pads 120a to 120d are formed at the ends of the pieces of wiring 112a to 112d, respectively, in the region 20 of the circuit board 11 illustrated in FIG. 9. Further, the groove-shaped pad opening 113B for transversely exposing the pads 120a to 120d is formed on the resist part 113 formed above the main face 111A of the base material 111. Then, circulation grooves 133a to 133c are formed in a direction orthogonal to the direction in which the groove-shaped pad opening 113A is formed, and are connected to the pad opening 113A. Further, a circulation groove 133d is formed in parallel with the direction in which the groove-shaped pad opening 113A is formed, and is connected to an end 113D of the pad opening 113A. Further, the imaging device 12 is provided at a position where the bumps 14 oppose the pads 120 on the main face 111A of the base material 111. The two-dot chain line 1200 indicates a peripheral end face when the imaging device 12 is flip-chip mounted.

The encapsulation resin 15 can flow less near the end of the groove-shaped pad opening 113A than at other parts of the pad opening 113A. Thus, the circulation groove 133d is provided at the end 113D of the pad opening 113A thereby to flow more encapsulation resin 15 at the end of the pad opening 113A.

The first embodiment of the present disclosure has been described above.

3. Second Embodiment

A second embodiment of the present disclosure will be described below.

3.1. Schematic Configuration of Camera Module

Figure 10:
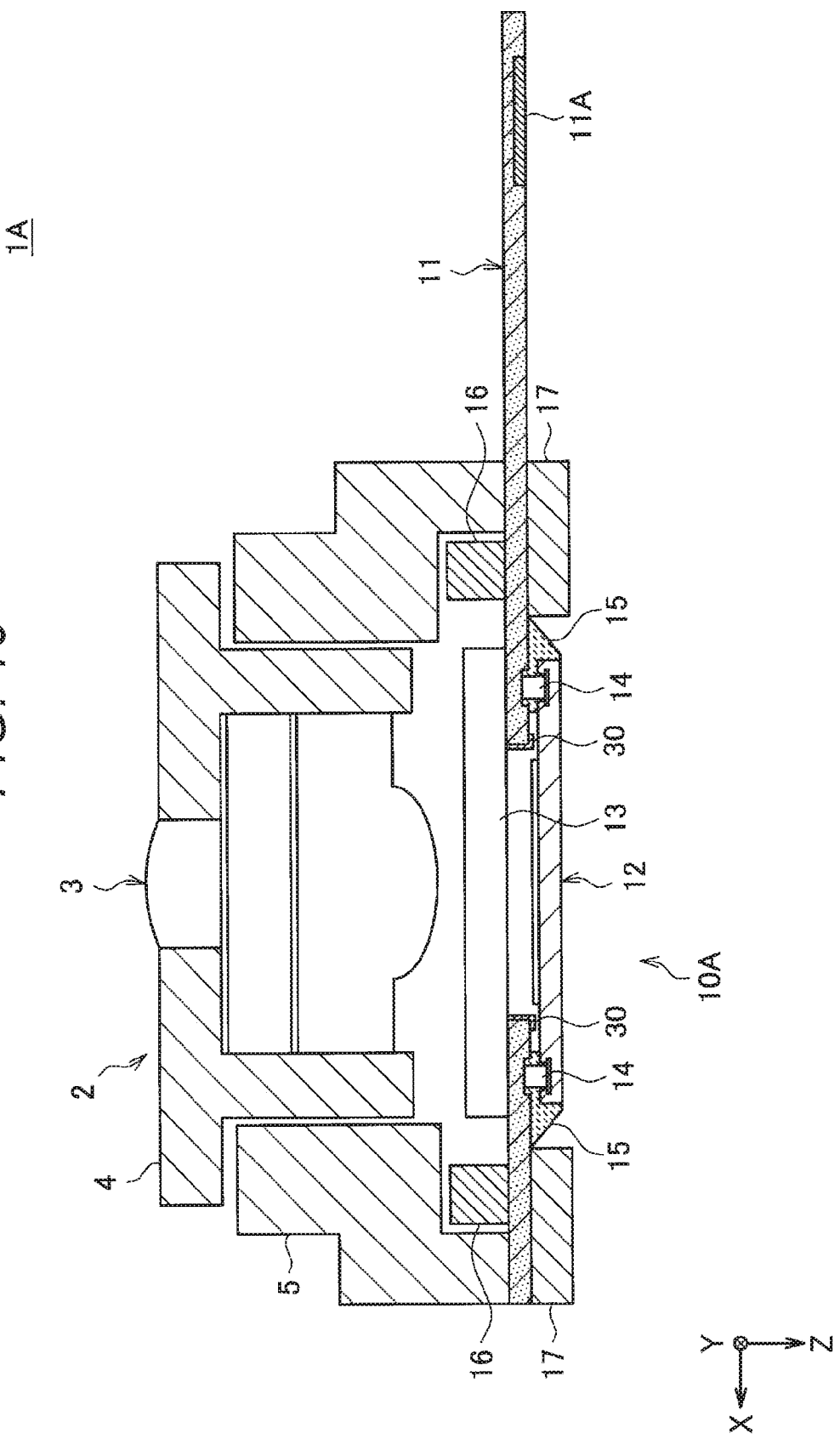
FIG. 10 is a cross-section view illustrating a schematic configuration of a camera module according to a second embodiment of the present disclosure.

FIG. 10 is a cross-section view illustrating a schematic configuration of a camera module 1A according to a second embodiment of the present disclosure. As illustrated in FIG. 10, the camera module 1A includes the lens unit 2, an electronic component 10A, and the reinforcement plate 17. The configurations and functions of the lens unit 2 and the reinforcement plate 17 according to the present embodiment are similar to those in the first embodiment, and thus the description thereof will be omitted.

The electronic component 10A according to the present embodiment includes the circuit board 11, the imaging device 12, the translucent member 13, the bumps 14, the encapsulation resin 15, the passive component 16, and a dam part 30. The electronic component 10A according to the present embodiment is different from the electronic component 10 according to the first embodiment in that it has the dam part 30.

3.2. Configuration of Electronic Component

Figure 11:
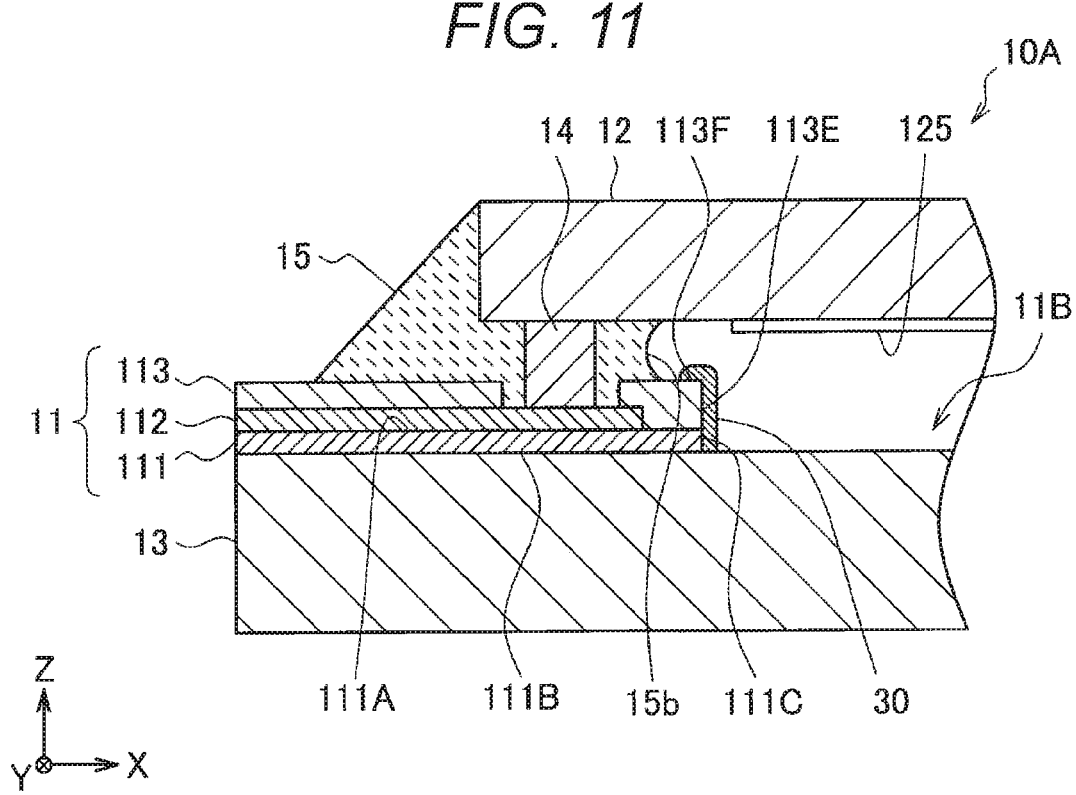
FIG. 11 is a cross-section view illustrating an exemplary configuration of an electronic component according to the embodiment.

An exemplary configuration of the electronic component 10A according to the present embodiment will be described below. FIG. 11 is a cross-section view illustrating an exemplary configuration of the electronic component 10A according to the present embodiment. Additionally, the configuration of the passive component 16 is omitted from FIG. 11.

As illustrated in FIG. 11, the electronic component 10A includes the circuit board 11, the imaging device 12, the translucent member 13, the bumps 14, the encapsulation resin 15, and the dam part 30. The functions of the circuit board 11, the imaging device 12, the translucent member 13, the bumps 14, and the encapsulation resin 15 according to the present embodiment are similar to those in the first embodiment, and thus the description thereof will be omitted.

According to the present embodiment, the dam part 30 is formed at the opening end face of the main opening 11B of the circuit board 11. The dam part 30 can be made of well-known resin.

The dam part 30 according to the present embodiment is formed to protrude from the upper face (surface) 113F of the resist part 113 at least in side view along an opening peripheral end 113E of the main opening 11B of the resist part 113. That is, the top of the dam part 30 is positioned above the upper face 113F of the resist part 113. In the example illustrated in FIG. 11, the dam part 30 is adhered on the upper face of the resist part 113.

When the encapsulation resin 15 is filled between the circuit board 11 and the imaging device 12 along the above-described circulation grooves 130, the encapsulation resin 15 may reach the main opening 11B of the circuit board 11. In this case, the encapsulation resin 15 can invade the light receiving face 125 of the imaging device 12.

Thus, the dam part 30 is provided to protrude from the upper face 113F of the resist part 113 along the opening peripheral end 113E of the resist part 113, thereby damming the encapsulation resin 15 flowing toward the inside of the electronic component 10A. Therefore, the encapsulation resin 15 can be prevented from invading the light receiving face 125 of the imaging device 12 while filling around the bumps 14 like encapsulation resin 15b illustrated in FIG. 11.

Additionally, as illustrated in FIG. 11, the dam part 30 may be formed to cover the opening peripheral end 113E of the resist part 113 and an opening peripheral end 111C of the base material 111. With the configuration, the opening end faces can be protected and an occurrence of dust can be prevented.

Further, the dam part 30 may be made of absorbent resin. The resin may contain a black material such as carbon material, for example. Thereby, light to enter the opening peripheral end 111C of the base material 111 is absorbed. Thus, an occurrence of flare or ghost due to reflected light from the opening peripheral ends 111C can be restricted.

Figure 12:
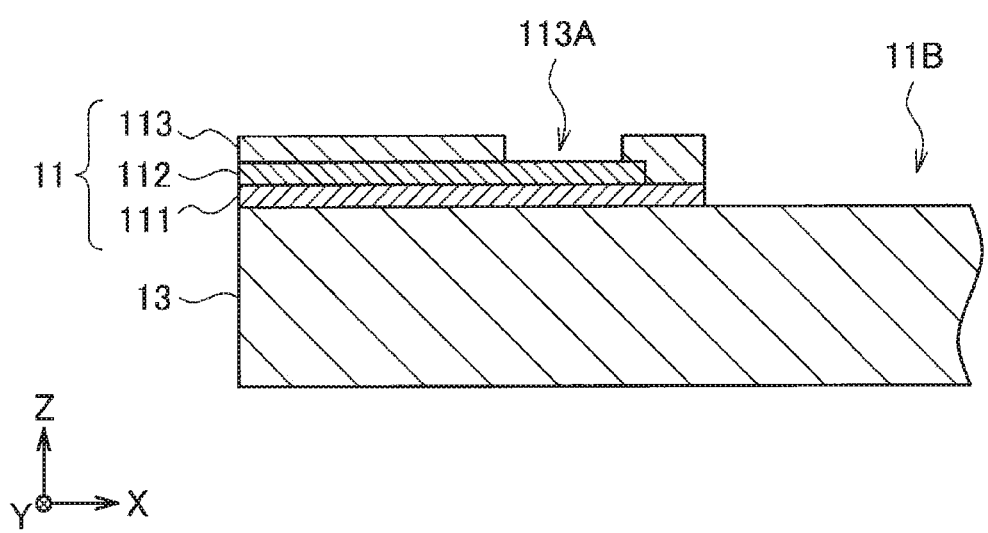
FIG. 12 is a cross-section view of the circuit board laterally viewed in a dam part forming step according to the embodiment.
Figure 13:
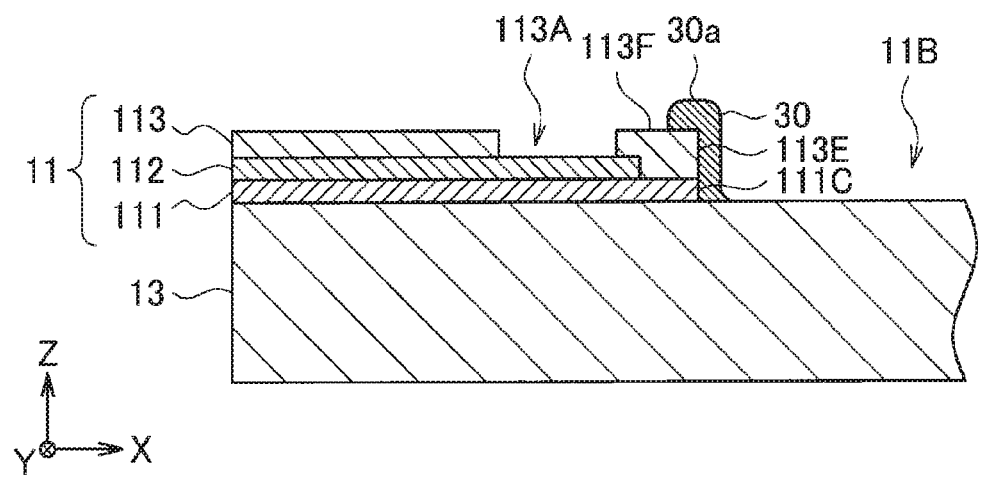
FIG. 13 is a cross-section view of the circuit board laterally viewed in the dam part forming step according to the embodiment.
Figure 14:
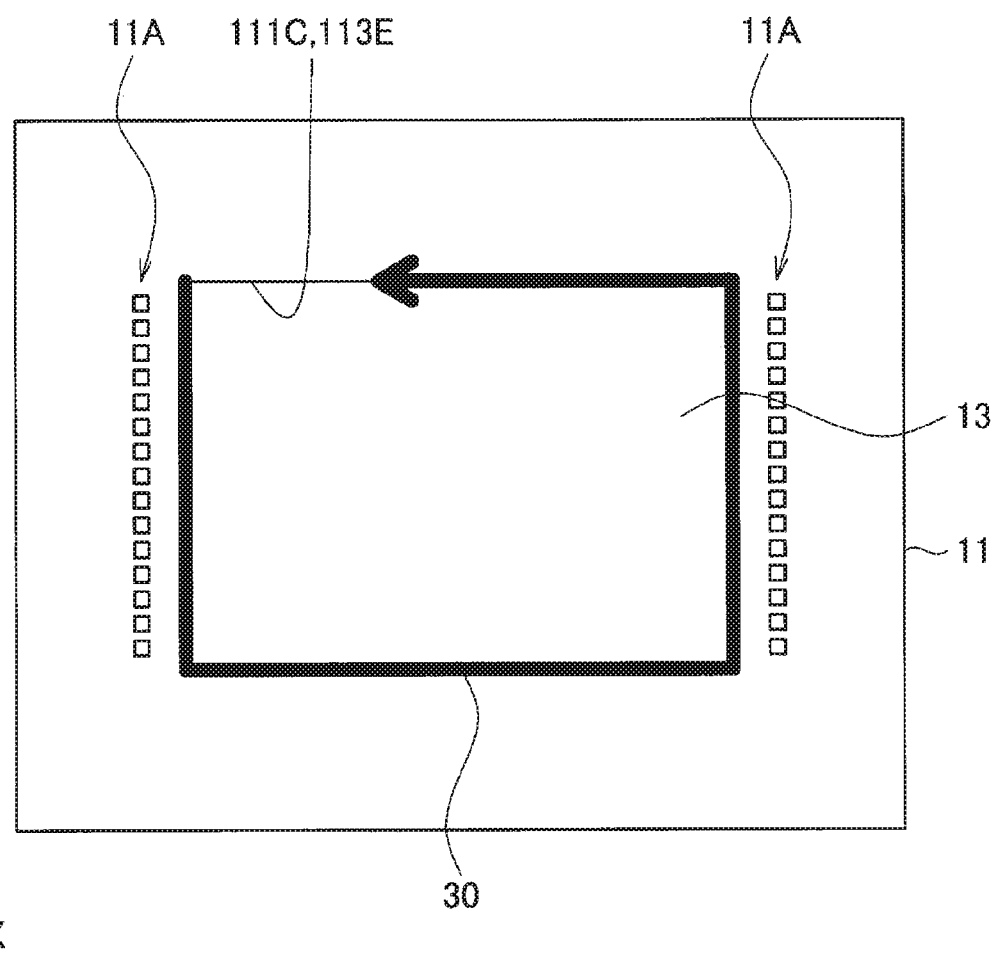
FIG. 14 is a diagram of the circuit board viewed from above in the dam part forming step according to the embodiment.

A method for forming the dam part 30 will be described below with reference to FIG. 12 to FIG. 14. FIG. 12 to FIG. 14 are schematic diagrams illustrating each exemplary step in the method for forming the dam part 30 according to the present embodiment. FIG. 12 and FIG. 13 are cross-section views of the circuit board 11 laterally viewed in the step of forming the dam part 30, and FIG. 14 is a diagram of the circuit board 11 viewed from above in the step of forming the dam part 30.

At first, the circuit board 11 and the translucent member 13 are previously bonded to each other as illustrated in FIG. 12. A pattern of the main opening 11B of the circuit board as well as the wiring 112 and the resist part 113 may be previously formed before or after the step of bonding the circuit board 11 and the translucent member 13.

As illustrated in FIG. 13 and FIG. 14, the dam part 30 is then formed along the opening peripheral end 113E of the main opening 11B of the resist part 113 and the opening peripheral end 111C of the main opening 11B of the base material 111. At this time, the dam part 30 is formed such that the top part 30a of the dam part 30 is positioned above the upper face 113F of the resist part 113 as illustrated in FIG. 13.

3.3. Variant

A variant of the present embodiment will be described below.

Figure 15:
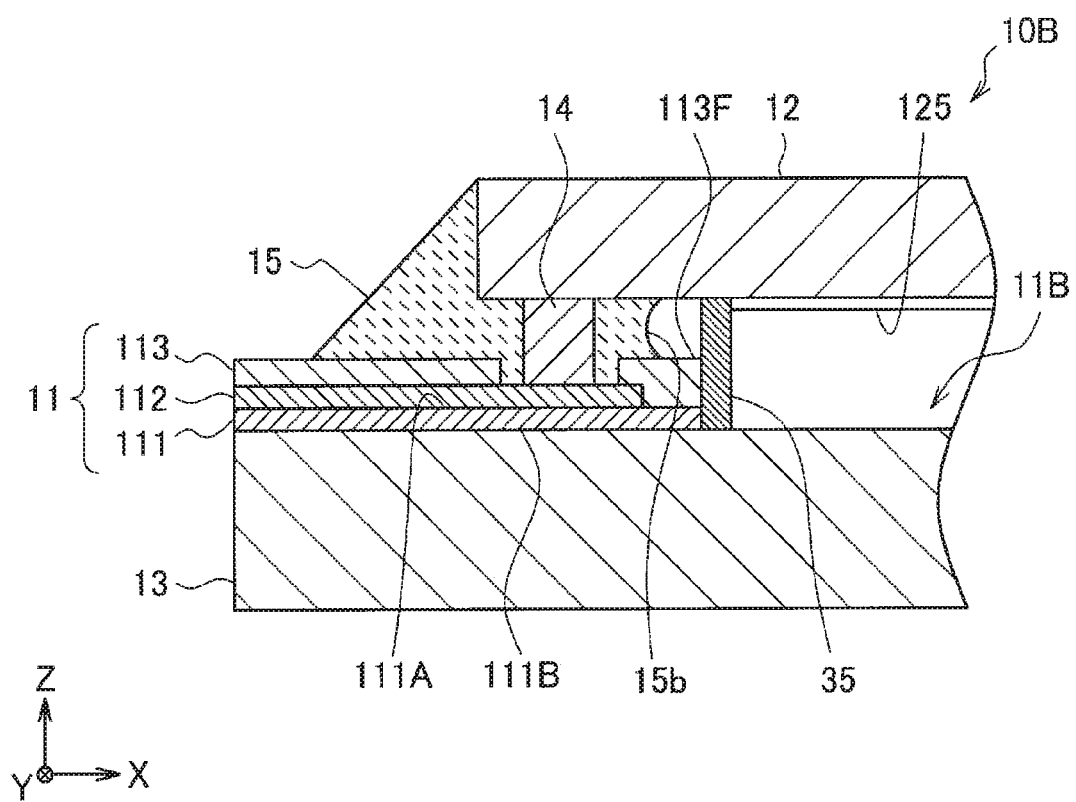
FIG. 15 is a cross-section view illustrating an exemplary configuration of an electronic component according to a variant of the embodiment.

FIG. 15 is a cross-section view illustrating an exemplary configuration of an electronic component 10B according to a variant of the present embodiment. A dam part 35 according to the present variant is formed to contact with the outside face of the light receiving face 125 of the imaging device 12.

Also in this case, the encapsulation resin 15 flowing toward the inside of the electronic component 10A can be dammed. Thus, the encapsulation resin 15 can be prevented from invading the light receiving face 125 of the imaging device 12 while filling around the bumps 14 like the encapsulation resin 15b illustrated in FIG. 15.

Additionally, the protrusion length from the upper face 113F of the resist part 113 (or the length between the upper face 113F of the resist part 113 and the top part 30a of the dam part in the lamination direction) is not particularly limited for the dam part 30 according to the present embodiment. As long as the dam part 30 protrudes from the upper face 113F of the resist part 113 and does not interfere with the imaging device 12 when the imaging device 12 is flip-chip mounted, the degree of protrusion of the dam part 30 is not particularly limited.

The second embodiment of the present disclosure has been described above.

4. Third Embodiment

A third embodiment of the present disclosure will be described below.

4.1. Schematic Configuration of Camera Module

Figure 16:
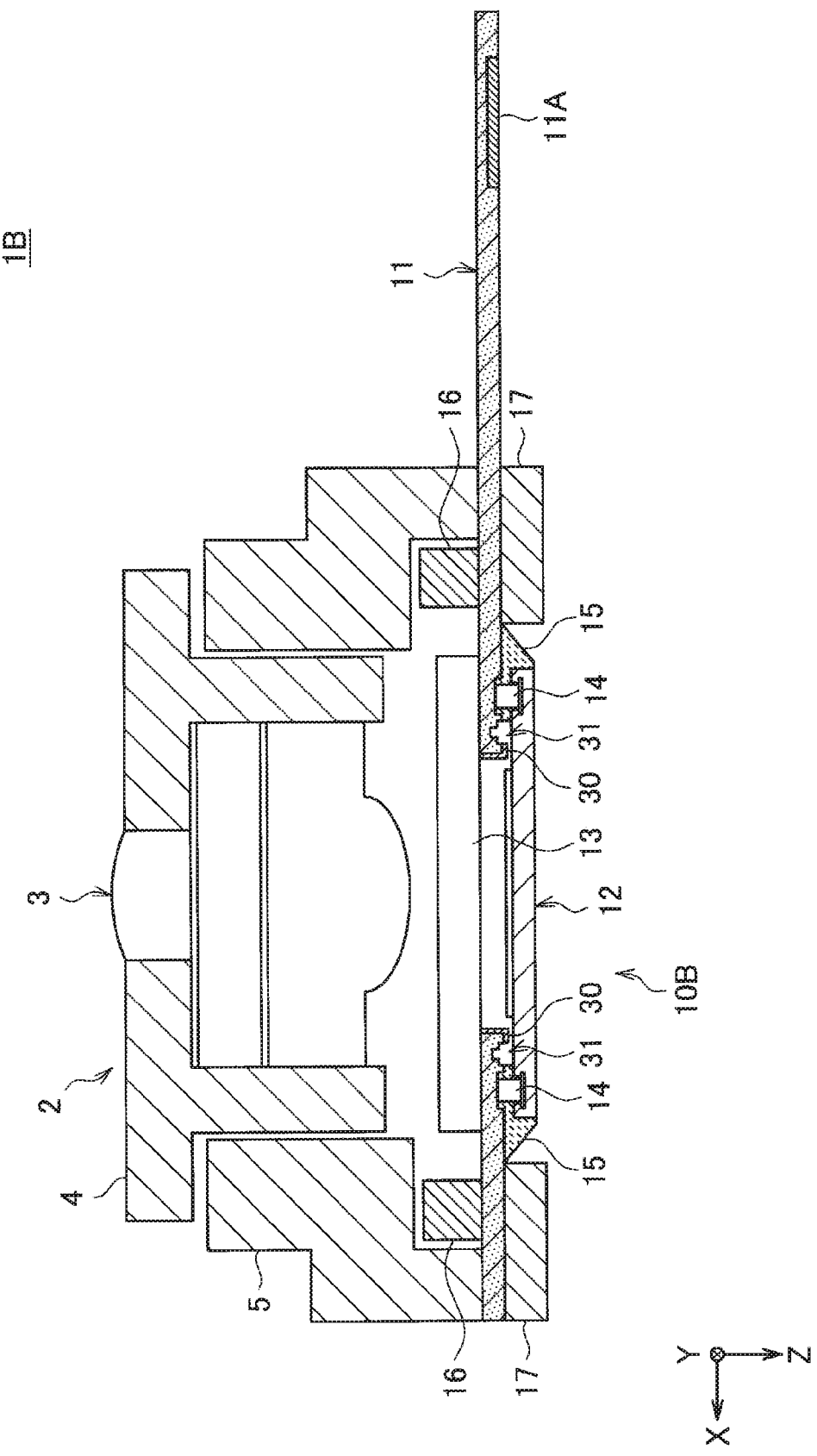
FIG. 16 is a cross-section view illustrating a schematic configuration of a camera module according to a third embodiment of the present disclosure.

FIG. 16 is a cross-section view illustrating a schematic configuration of a camera module 1B according to the third embodiment of the present disclosure. As illustrated in FIG. 16, the camera module 1B includes the lens unit 2, the electronic component 10B, and the reinforcement plate 17. The configurations and functions of the lens unit 2 and the reinforcement plate 17 according to the present embodiment are similar to those in the first embodiment, and thus the description thereof will be omitted.

The electronic component 10B according to the present embodiment includes the circuit board 11, the imaging device 12, the translucent member 13, the bumps 14, the encapsulation resin 15, the passive component 16, the dam part 30, and a trap part 31. The electronic component 10B according to the present embodiment is different from the electronic component 10A according to the second embodiment in that it further includes the trap part 31 (corresponding to a first trap part).

4.2. Configuration of Electronic Component

Figure 17:
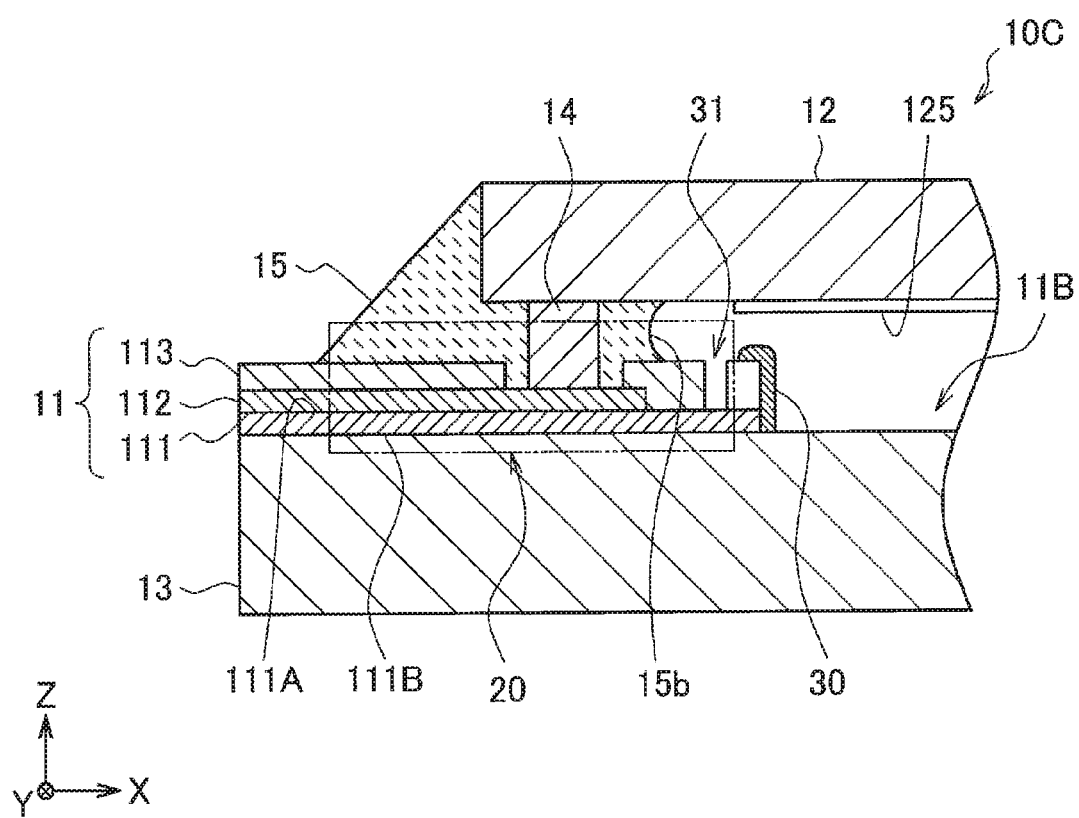
FIG. 17 is a cross-section view illustrating an exemplary configuration of an electronic component according to the embodiment.

An exemplary configuration of the electronic component 10B according to the present embodiment will be described below. FIG. 17 is a cross-section view illustrating an exemplary configuration of the electronic component 10B according to the present embodiment. Additionally, the configuration of the passive component 16 is omitted from FIG. 17.

As illustrated in FIG. 17, the electronic component 10B includes the circuit board 11, the imaging device 12, the translucent member 13, the bumps 14, the encapsulation resin 15, and the dam part 30. The functions of the respective constituents are similar to those in the second embodiment, and thus the description thereof will be omitted.

The trap part 31 is formed on the resist part 113 of the circuit board 11 according to the present embodiment. The groove-shaped trap part 31 is formed in a direction along the opening peripheral end of the main opening 11B.

Figure 18:
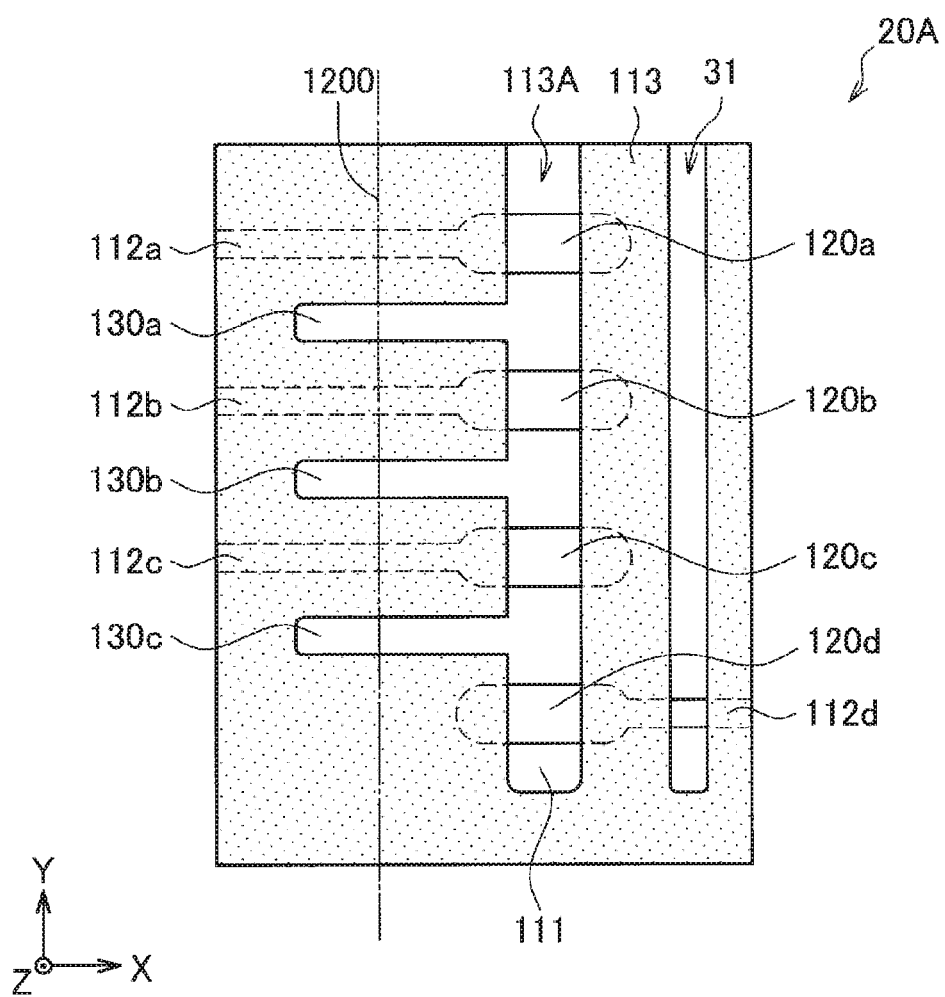
FIG. 18 is a top view of enlarged part of a circuit board according to the embodiment.

FIG. 18 is a top view of enlarged part of the circuit board 11 according to the present embodiment. The top view is a diagram of the circuit board 11 included in a region 20A in FIG. 17 viewed from above.

The pieces of wiring 112a to 112d are formed on the main face 111A of the base material 111 and the pads 120a to 120d are formed at the ends of the pieces of wiring 112a to 112d, respectively, in the region 20A of the circuit board 11 illustrated in FIG. 18. Further, the groove-shaped pad opening 113B for transversely exposing the pads 120a to 120d is formed on the resist part 113 formed above the main face 111A of the base material 111. The circulation grooves 130a to 130c are then formed in a direction orthogonal to the direction in which the groove-shaped pad opening 113A is formed, and are connected to the pad opening 113A. Further, the imaging device 12 is provided at a position where the bumps 14 oppose the pads 120 on the main face 111A of the base material 111. The two-dot chain line 1200 indicates a peripheral end face when the imaging device 12 is flip-chip mounted.

Further, the trap part 31 is provided between the pads 120 and the opening peripheral end 113E of the main opening 11B of the resist part 113 (not illustrated in FIG. 18, but present in the positive X-axis direction from the pad 120) in the resist part 113 according to the present embodiment.

The trap part 31 can be in a groove shape as illustrated in FIG. 18. The groove depth of the trap part 31 is not particularly limited, and the main face 111A of the base material 111 (or the wiring 112) may be exposed at the bottom of the trap part 31, for example. The trap part 31 is formed to extend in a direction along the opening peripheral end 113E (in the Y-axis direction in FIG. 18).

With the configuration, when the encapsulation res in 15 is filled between the circuit board 11 and the imaging device 12 along the circulation grooves 130, the encapsulation resin 15 further flowing from the pads 120 toward the main opening 11B can flow into the trap part 31. That is, the trap part 31 serves to dam the encapsulation resin 15 flowing toward the main opening 11B. Thereby, the encapsulation resin 15 can be prevented from invading the light receiving face 125 of the imaging device 12 while filling around the bumps 14 like the encapsulation resin 15b illustrated in FIG. 17.

Additionally, the configuration of the trap part 31 illustrated in FIG. 18 is merely exemplary. As long as the trap part 31 is formed in a groove shape in a direction along the opening peripheral end 113E between the pads 120 and the opening peripheral end 113E of the main opening 11B of the resist part 113, the size, the groove depth, and the formation position of the trap part 31 are not particularly limited. Further, the position where the trap part 31 is installed according to the present embodiment is not limited to between the pad opening 113A for exposing the pads 120 and the opening peripheral end 113E of the main opening 11B.

Figure 19:
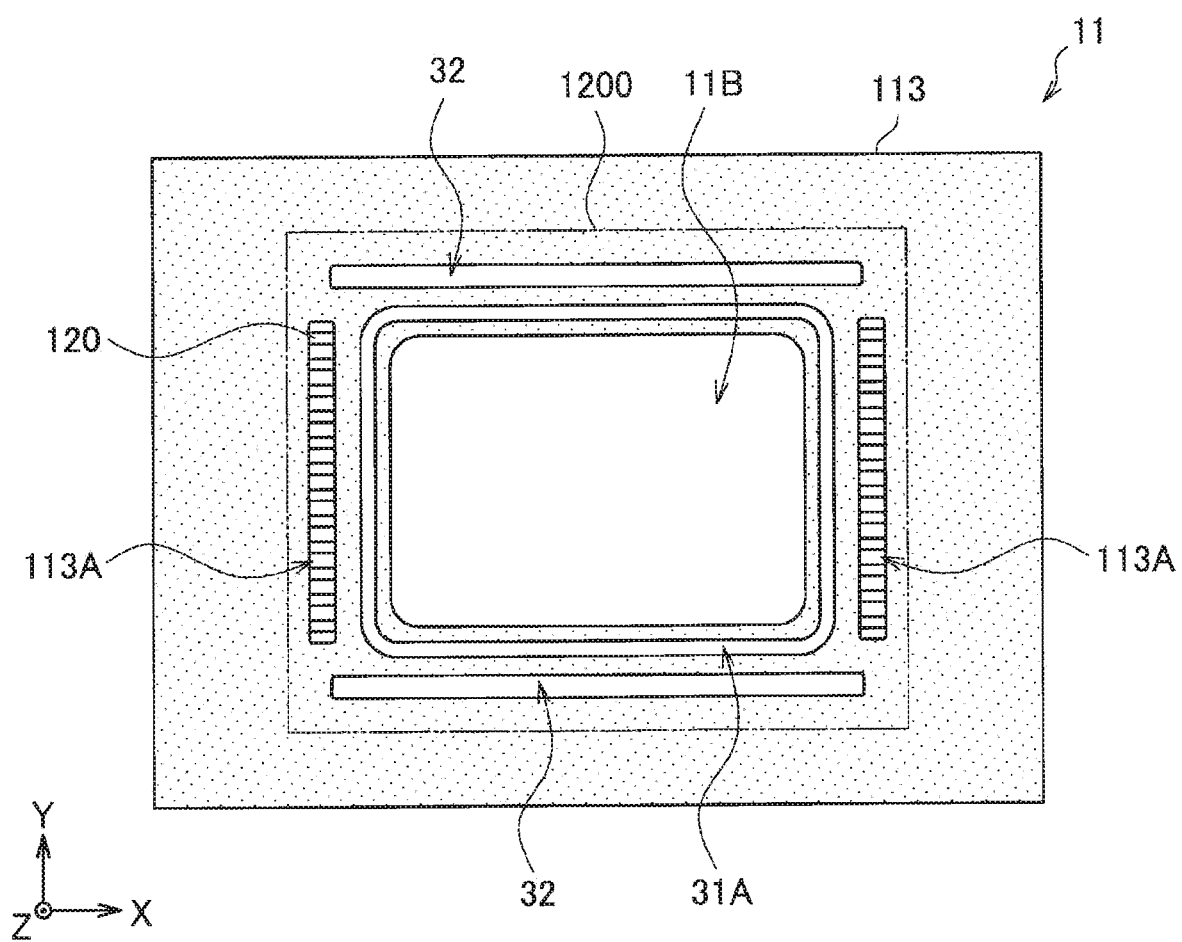
FIG. 19 is a top view illustrating a schematic configuration of the circuit board according to a variant of the embodiment.

FIG. 19 is a top view illustrating a schematic configuration of the circuit board 11 according to a variant of the present embodiment. Additionally, the configurations of the circulation grooves 130 and the like are omitted from FIG. 19. As illustrated in FIG. 19, a trap part 31A may be a groove annularly formed around the opening peripheral end 113E of the main opening 11B of the circuit board 11 in the resist part 113, for example. In this case, even in a case where the encapsulation resin 15 is filled in a part where the pads 120 are not provided in the base material 111, the encapsulation resin 15 can be prevented from flowing into the main opening 11B.

Further, as illustrated in FIG. 19, other trap part 32 (corresponding to a second trap part) may be provided on the resist part 113 at a part where the pad opening 113A is not provided in the resist part 113. In the example illustrated in FIG. 19, the groove-shaped trap part 32 may be formed in a direction along the boundary of the region 1200 outside the trap part 31 and within the region 1200 corresponding to the imaging device 12 in plan view. Thereby, the flowing behavior of the encapsulation resin 15 can be similar in the part in a case where the encapsulation resin 15 is filled from the part where the pad opening 113A is provided and in a case where the encapsulation resin 15 is filled from the part where the trap part 32 is provided. Therefore, uneven filling of the encapsulation resin 15 can be restricted. Additionally, the trap part 32 can be formed on the resist part 113 even in a case where the trap part 31 does not need to be provided. That is, the trap part 32 is provided so that uneven filling of the encapsulation resin 15 can be restricted also in a chip in which the main opening 11B of the circuit board 11 is not provided.

4.3. Variant

Figure 20:
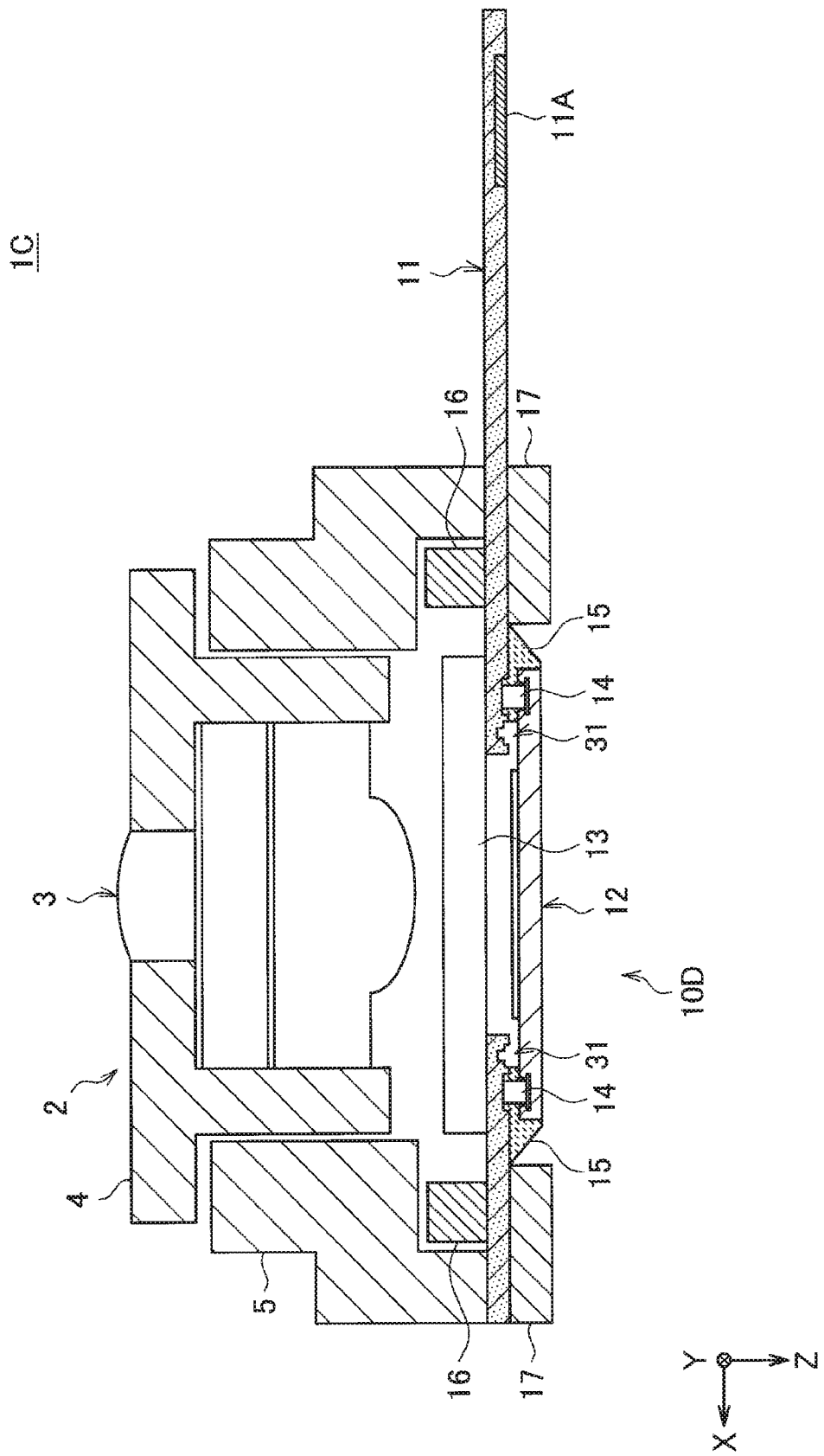
FIG. 20 is a cross-section view illustrating a schematic configuration of a camera module according to a variant of the embodiment.

FIG. 20 is a cross-section view illustrating a schematic configuration of a camera module 1C according to a variant of the present embodiment. As illustrated in FIG. 20, the camera module 1C includes the lens unit 2, an electronic component 10D, and the reinforcement plate 17. The configurations and functions of the lens unit 2 and the reinforcement plate 17 according to the present variant are similar to those in the first embodiment, and thus the description thereof will be omitted.

The electronic component 10C according to the present variant includes the circuit board 11, the imaging device 12, the translucent member 13, the bumps 14, the encapsulation resin 15, the passive component 16, and the trap part 31. The electronic component 10C according to the present variant is different from the electronic component 10B according to the present embodiment in that it does not include the dam part 30.

Even in a case where the electronic component 10C does not include the dam part 30, the function of the above-described trap part 31 can be achieved. That is, when the encapsulation resin 15 is filled between the circuit board 11 and the imaging device 12 along the circulation grooves 130, the encapsulation resin 15 further flowing from the pads 120 toward the main opening 11B can flow into the trap part 31. Thereby, the encapsulation resin 15 can be prevented from invading the light receiving face 125 of the imaging device 12 while filling around the bumps 14.

Additionally, even in a case where the encapsulation resin 15 is filled in the trap part 31 and the encapsulation resin 15 further flows toward the main opening 11B, the encapsulation resin 15 can be prevented from invading the light receiving face 125 by the dam part 30 in the electronic component 10B according to the present embodiment.

The third embodiment has been described above.

5. Application to In-Vivo Information Acquisition System

The technology according to the present disclosure (the present technology) can be applied to various products. For example, the technology according to the present disclosure may be applied to an endoscopic surgery system.

Figure 21:
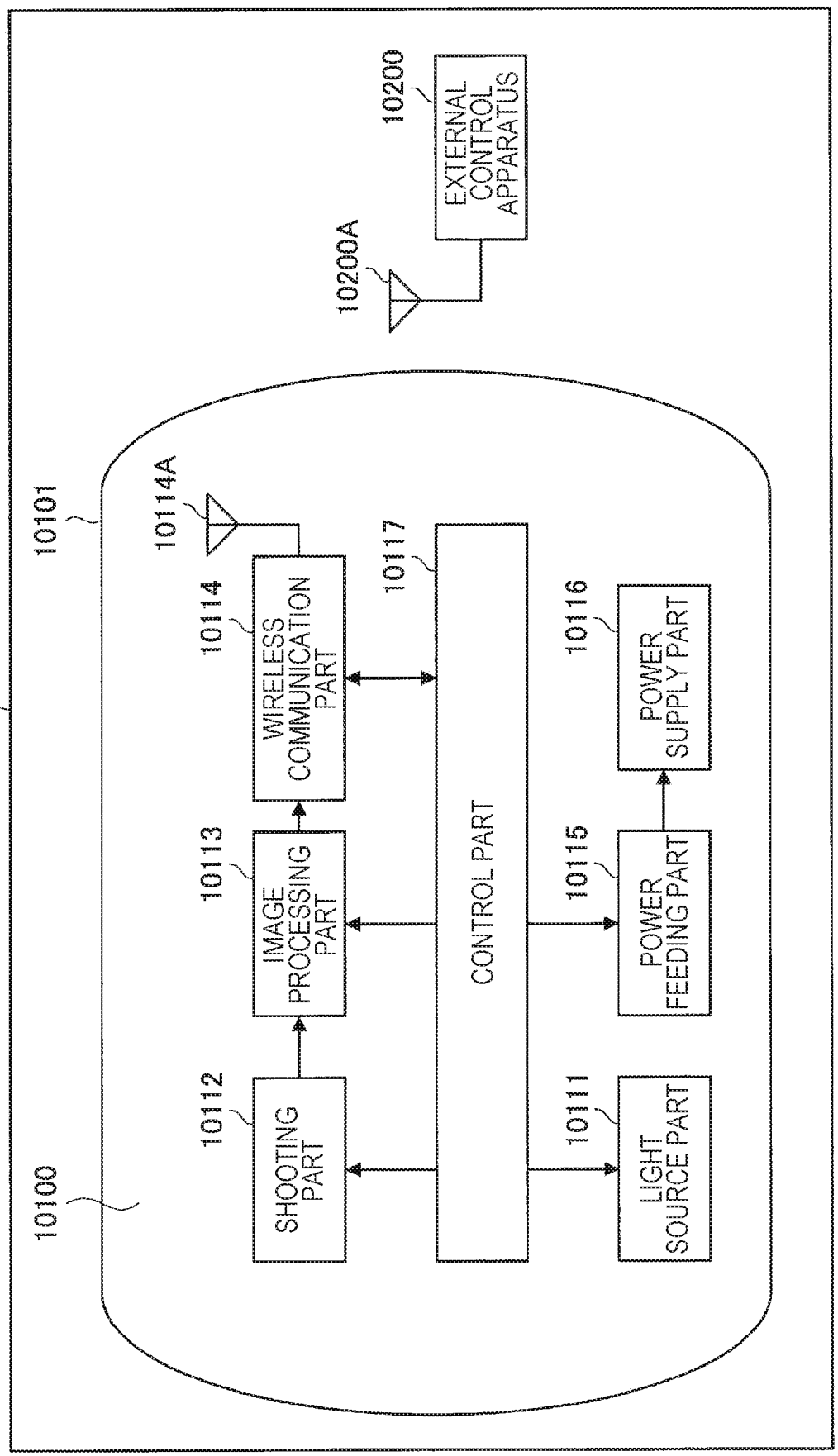
FIG. 21 is a block diagram illustrating an exemplary schematic configuration of an in-vivo information acquisition system.

FIG. 21 is a block diagram illustrating an exemplary schematic configuration of a patient's in-vivo information acquisition system by use of a capsule endoscope to which the technology according to the present disclosure (the present technology) is applicable.

An in-vivo information acquisition system 10001 is configured of a capsule endoscope 10100 and an external control apparatus 10200.

The capsule endoscope 10100 is swallowed by a patient on examination. The capsule endoscope 10100 has a shooting function and a wireless communication function, and sequentially shoots images of the inside of organs (also denoted as in-vivo image) at predetermined intervals and sequentially and wirelessly transmits the information indicating the in-vivo images to the external control apparatus 10200 outside the body while moving through the organs such as stomach and intestines by peristalsis or the like until it is naturally expelled from the patient.

The external control apparatus 10200 totally controls the operations of the in-vivo information acquisition system 10001. Further, the external control apparatus 10200 receives the information indicating the in-vivo images transmitted from the capsule endoscope 10100, and generates image data for displaying the in-vivo images on a display apparatus (not illustrated) on the basis of the received information indicating the in-vivo images.

The in-vivo information acquisition system 10001 can acquire the in-vivo images shooting the inside of the patient's body as needed in this way until the capsule endoscope 10100 is expelled after it is swallowed.

The configurations and functions of the capsule endoscope 10100 and the external control apparatus 10200 will be described in more detail.

The capsule endoscope 10100 includes a capsule casing 10101, and the casing 10101 houses a light source part 10111, a shooting part 10112, an image processing part 10113, a wireless communication part 10114, a power feeding part 10115, a power supply part 10116, and a control part 10117 therein.

The light source part 10111 is configured of, for example, a light source such as light emitting diode (LED), and irradiates a shooting field of the shooting part 10112 with light.

The shooting part 10112 is configured of an optical system including an imaging device and a plurality of lenses provided in front of the imaging device. Reflected light of light (denoted as observation light below) with which a body tissue as an object to be observed is irradiated is collected by the optical system and enters the imaging device. The observation light entering the imaging device is photoelectrically converted and an image signal corresponding to the observation light is generated in the shooting part 10112. The image signal generated by the shooting part 10112 is provided to the image processing part 10113.

The image processing part 10113 is configured of a processor such as central processing unit (CPU) or graphics processing unit (GPU), and performs various signal processing on the image signal generated by the shooting part 10112. The image processing part 10113 provides the image signal subjected to a signal processing as RAW data to the wireless communication part 10114.

The wireless communication part 10114 performs a predetermined processing such as modulation processing on the image signal subjected to the signal processing by the image processing part 10113, and transmits the image signal to the external control apparatus 10200 via an antenna 10114A. Further, the wireless communication part 10114 receives a control signal for driving and controlling the capsule endoscope 10100 from the external control apparatus 10200 via the antenna 10114A. The wireless communication part 10114 provides the control signal received from the external control apparatus 10200 to the control part 10117.

The power feeding part 10115 is configured of a power reception antenna coil, a power regeneration circuit for regenerating power from a current generated in the antenna coil, a booster circuit, and the like. The power feeding part 10115 generates power by use of the non-contact charging principle.

The power supply part 10116 is configured of a secondary battery, and accumulates power generated by the power feeding part 10115. The arrows and the like indicating the destinations of power supplied from the power supply part 10116 are omitted in FIG. 21 in order to avoid the complicated diagram, but the power accumulated in the power supply part 10116 is supplied to the light source part 10111, the shooting part 10112, the image processing part 10113, the wireless communication part 10114, and the control part 10117, and is used to drive the parts.

The control part 10117 is configured of a processor such as CPU, and controls driving the light source part 10111, the shooting part 10112, the image processing part 10113, the wireless communication part 10114, and the power feeding part 10115 as needed according to a control signal transmitted from the external control apparatus 10200.

The external control apparatus 10200 is configured of a processor such as CPU or GPU, a microcomputer on which storage devices such as processor and memory are mounted together, a control board, or the like. The external control apparatus 10200 transmits a control signal to the control part 10117 in the capsule endoscope 10100 via an antenna 10200A, thereby controlling the operations of the capsule endoscope 10100. For example, the conditions for irradiating an object to be observed in the light source part 10111 with light can be changed by a control signal from the external control apparatus 10200 in the capsule endoscope 10100. Further, the shooting conditions (such as frame rate and exposure value in the shooting part 10112, for example) can be changed by a control signal from the external control apparatus 10200. Further, the processing contents in the image processing part 10113 and the conditions (such as transmission interval and number of images to be transmitted, for example) for transmitting an image signal in the wireless communication part 10114 may be changed by a control signal from the external control apparatus 10200.

Further, the external control apparatus 10200 performs various image processing on the image signal transmitted from the capsule endoscope 10100, and generates image data for displaying the shot in-vivo images on the display apparatus. For the image processing, various signal processing such as development processing (demosaic processing), image quality increase processing (bandwidth emphasis processing, super-resolution processing, noise reduction (NR) processing and/or blurring correction processing, for example), and/or enlargement processing (electronic zooming processing) can be performed, for example. The external control apparatus 10200 controls driving the display apparatus, and causes it to display the shot in-vivo images on the basis of the generated image data. Alternatively, the external control apparatus 10200 may cause a recording apparatus (not illustrated) to record the generated image data or may cause a printing apparatus (not illustrated) to print out the generated image data.

An exemplary in-vivo information acquisition system to which the technology according to the present disclosure is applicable has been described above. The technology according to the present disclosure is applicable to the shooting part 10112 in the above-described constituents. Specifically, the camera module 1 according to each embodiment described above can be applied to the shooting part 10112. The technology according to the present disclosure is applied to the shooting part 10112, and thus the shooting part 10112 can be stably used for a long time.

6. Application to Endoscopic Surgery System

Further, the technology according to the present disclosure (the present technology) is applicable to various products. For example, the technology according to the present disclosure may be applied to an endoscopic surgery system.

Figure 22:
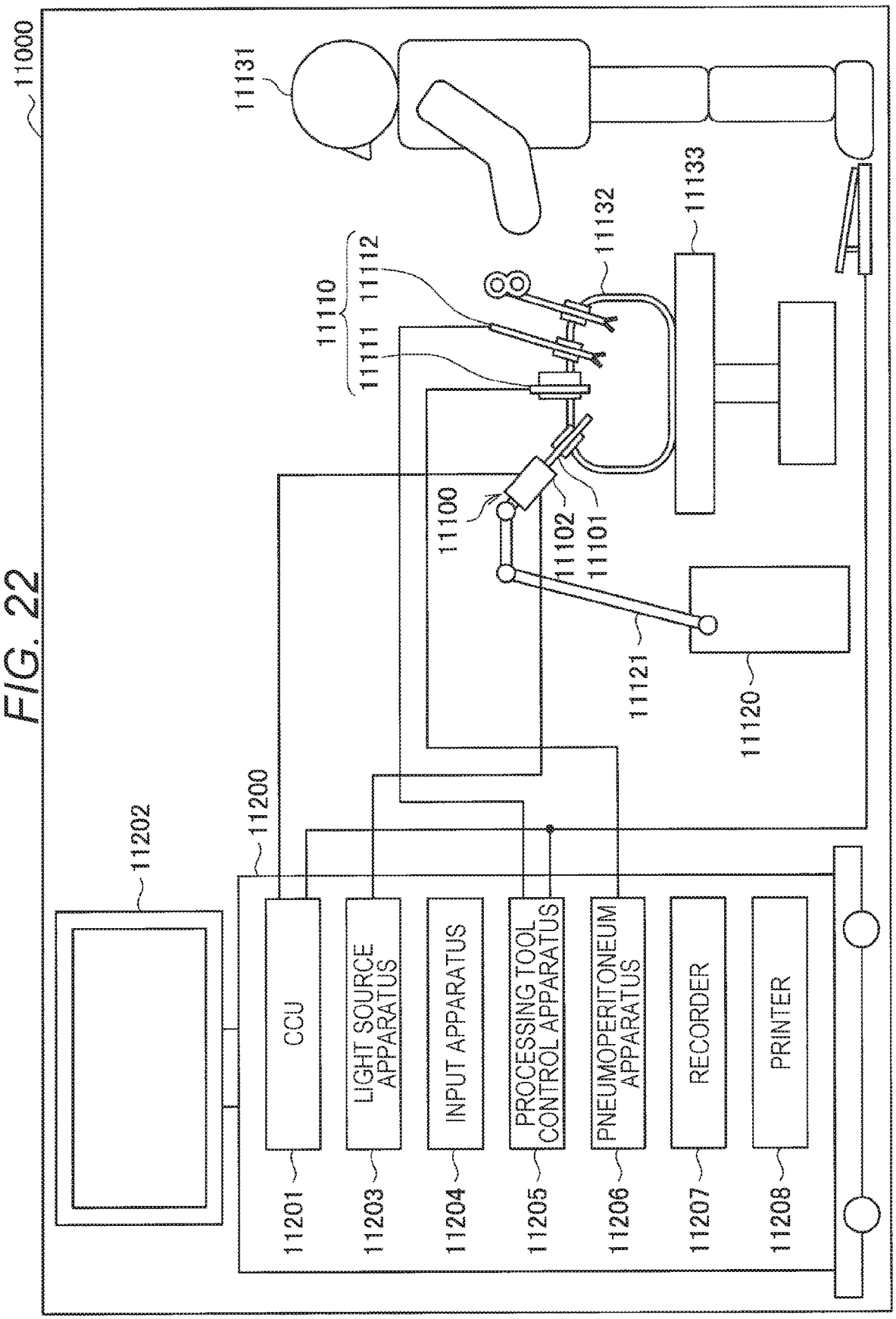
FIG. 22 is a diagram illustrating an exemplary schematic configuration of an endoscopic surgery system.

FIG. 22 is a diagram illustrating an exemplary schematic configuration of an endoscopic surgery system to which the technology according to the present disclosure (the present technology) can be applied.

FIG. 22 illustrates how an operator (doctor) 11131 performs an operation on a patient 11132 on a patient's bed 11133 by use of an endoscopic surgery system 11000. As illustrated, the endoscopic surgery system 11000 is configured of an endoscope 11100, the other surgical instruments 11110 such as pneumoperitoneum tube 11111 and energy treatment tool 11112, a support arm apparatus 11120 for supporting the endoscope 11100, and a cart 11200 on which various apparatuses for endoscopic surgery are mounted.

The endoscope 11100 is configured of a lens tube 11101 the region of which at a predetermined length from the tip is inserted into the body cavity of the patient 11132, and a camera head 11102 connected to the base of the lens tube 11101. In the illustrated example, the endoscope 11100 configured as a rigid scope having the hard lens tube 11101 is illustrated, but the endoscope 11100 may be configured as a flexible scope having a flexible lens tube.

An opening with an objective lens fitted is provided at the tip of the lens tube 11101. A light source apparatus 11203 is connected to the endoscope 11100, and light generated by the light source apparatus 11203 is guided to the tip of the lens tube by a light guide extending into the lens tube 11101, and is applied toward an object to be observed in the body cavity of the patient 11132 via the objective lens. Additionally, the endoscope 11100 may be a direct-viewing lens, or may be an oblique-viewing lens or side-viewing lens.

An optical system and an imaging device are provided inside the camera head 11102, and reflected light (observation light) from an object to be observed is condensed on the imaging device via the optical system. The observation light is photoelectrically converted by the imaging device, and an electric signal corresponding to the observation light, or an image signal corresponding to the observed image is generated. The image signal is transmitted as RAW data to a camera control unit (CCU) 11201.

The CCU 11201 is configured of a central processing unit (CPU), a graphics processing unit (GPU), or the like, and totally controls the operations of the endoscope 11100 and a display apparatus 11202. Further, the CCU 11201 receives an image signal from the camera head 11102, and performs various image processing for displaying an image based on the image signal, such as development processing (demosaic processing), for example, on the image signal.

The display apparatus 11202 displays the image based on the image signal subjected to the image processing by the CCU 11201 under control of the CCU 11201.

The light source apparatus 11203 is configured of, for example, a light source such as light emitting diode (LED), and supplies irradiation light to the endoscope 11100 when shooting a surgical site or the like.

An input apparatus 11204 is an input interface for the endoscopic surgery system 11000. A user can input various items of information or instructions into the endoscopic surgery system 11000 via the input apparatus 11204. For example, the user inputs an instruction to change shooting conditions (such as kind of irradiation light, magnification, and focal distance) of the endoscope 11100 or the like.

A processing tool control apparatus 11205 controls to drive the energy treatment tool 11112 for cauterizing or cutting a tissue, sealing a blood vessel, and the like. A pneumoperitoneum apparatus 11206 feeds gas into the body cavity via the pneumoperitoneum tube 11111 to expand the body cavity of the patient 11132 in order to secure the field of view of the endoscope 11100 and to secure a working space of the operator. A recorder 11207 is an apparatus capable of recording various items of information regarding a surgery. A printer 11208 is an apparatus capable of printing various items of information regarding a surgery in various forms such as text, image, or graph.

Additionally, the light source apparatus 11203 for supplying irradiation light to the endoscope 11100 when shooting a surgical site can be configured of a white light source made of an LED, a laser light source, or a combination thereof, for example. In a case where the white light source is configured in a combination of RGB laser light sources, the output intensity and the output timing of each color (each wavelength) can be controlled with high accuracy, and thus the white balance of a shot image can be adjusted in the light source apparatus 11203. Further, in this case, an object to be observed is irradiated with beams of laser light from the respective RGB laser light sources in a time division manner, and the imaging device in the camera head 11102 is controlled to be driven in synchronization with the irradiation timings, thereby shooting the images corresponding to RGB in a time division manner. According to the method, a color image can be obtained without a color filter in the imaging device.

Further, the light source apparatus 11203 may be controlled to be driven for changing the intensity of light to be output at a predetermined time. The imaging device in the camera head 11102 is controlled to be driven in synchronization with the timings to change the intensities of the beams of light thereby to obtain images in a time division manner, and the images are combined thereby to generate an image with a high dynamic range without blocked-up shadows and blown-out highlights.

Further, the light source apparatus 11203 may be configured to supply light in a predetermined wavelength band corresponding to special light observation. Under the special light observation, for example, light in a narrower band than irradiation light (or white light) during normal observation is applied by use of the wavelength dependency of absorption of light in a body tissue, thereby performing narrow band imaging for shooting a predetermined tissue such as blood vessel in the superficial portion of the mucous membrane at high contrast. Alternatively, under the special light observation, fluorescent observation for obtaining an image by fluorescence caused by irradiation of excitation light may be performed. Under the fluorescent observation, a body tissue can be irradiated with excitation light thereby to observe fluorescence from the body tissue (autofluorescence observation), a reagent such as indocyanine green (ICG) can be locally injected into a body tissue, and the body tissue can be irradiated with excitation light corresponding to the fluorescent wavelength of the reagent thereby to obtain a fluorescent image, for example. The light source apparatus 11203 can be configured to supply a narrowband light and/or excitation light corresponding to the special light observation.

Figure 23:
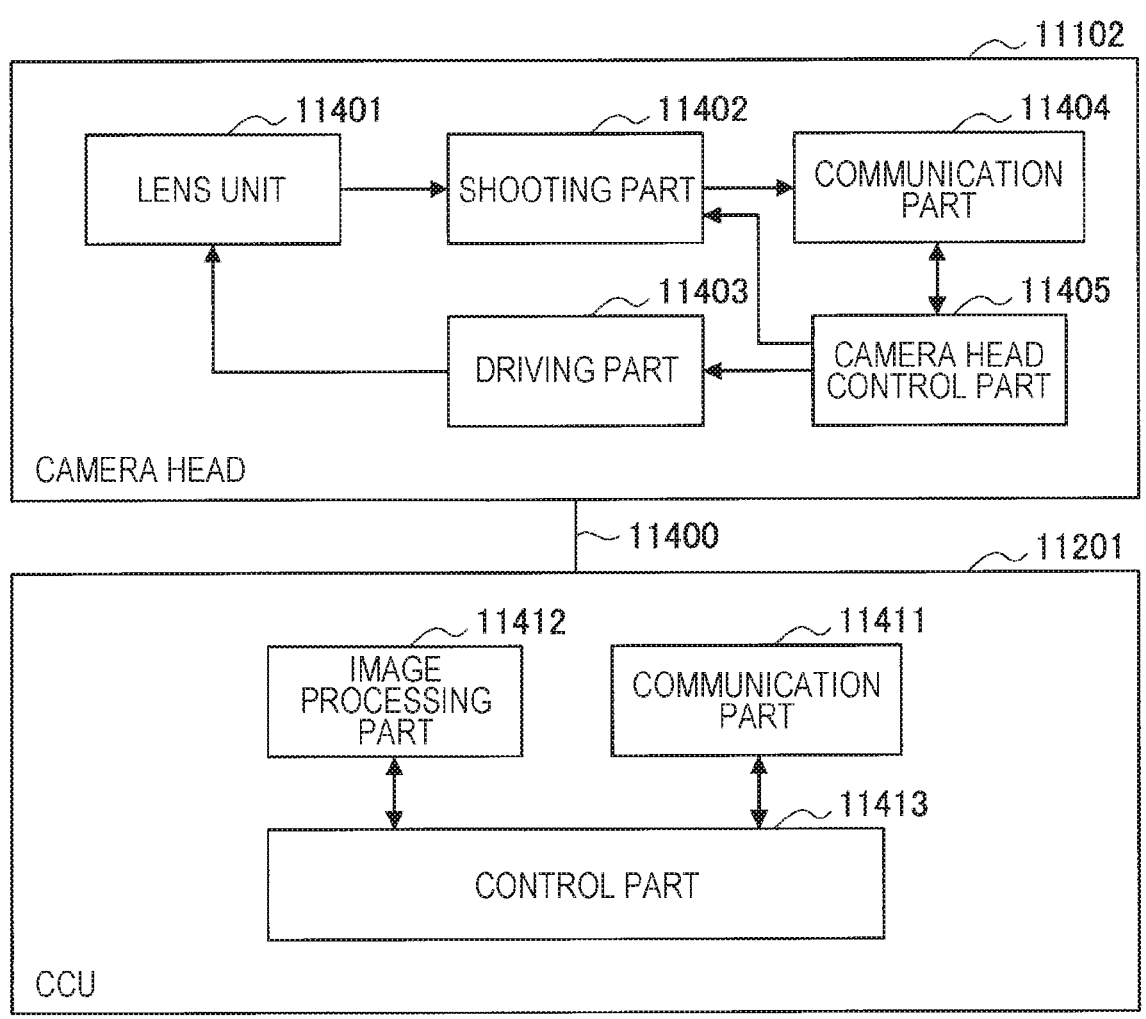
FIG. 23 is a block diagram illustrating an exemplary functional configuration of a camera head and a CCU.

FIG. 23 is a block diagram illustrating an exemplary functional configuration of the camera head 11102 and the CCU 11201 illustrated in FIG. 22.

The camera head 11102 has a lens unit 11401, a shooting part 11402, a driving part 11403, a communication part 11404, and a camera head control part 11405. The CCU 11201 has a communication part 11411, an image processing part 11412, and a control part 11413. The camera head 11102 and the CCU 11201 are communicably connected to each other via a transmission cable 11400.

The lens unit 11401 is an optical system provided at the connection part to the lens tube 11101. An observation light taken from the tip of the lens tube 11101 is guided to the camera head 11102, and is incident into the lens unit 11401. The lens unit 11401 is configured in a combination of a plurality of lenses including a zoom lens and a focus lens.

The shooting part 11402 is configured of an imaging device. One imaging device (or single plate) or a plurality of imaging devices (or multiplate) may configure the shooting part 11402. In a case where the shooting part 11402 is configured in multiplate, the image signals corresponding to RGB may be generated by the imaging devices, respectively, and combined thereby to obtain a color image, for example. Alternatively, the shooting part 11402 may have a pair of imaging devices for obtaining right-eye and left-eye image signals for 3 dimensional (D) display. 3D display is performed so that the operator 11131 can more accurately grasp the depth of a body tissue at a surgical site. Additionally, in a case where the shooting part 11402 is configured in multiplate, a plurality of lens units 11401 corresponding to the imaging devices can be provided, respectively.

Further, the shooting part 11402 may not necessarily be provided in the camera head 11102. For example, the shooting part 11402 may be provided immediately behind the objective lens inside the lens tube 11101.

The driving part 11403 is configured of an actuator, and moves the zoom lens and the focus lens in the lens unit 11401 by a predetermined distance along the optical axis under control of the camera head control part 11405. Thereby, the magnification and the focal point of an image shot by the shooting part 11402 can be adjusted as needed.

The communication part 11404 is configured of a communication apparatus for exchanging various items of information with the CCU 11201. The communication part 11404 transmits an image signal obtained from the shooting part 11402 as RAW data to the CCU 11201 via the transmission cable 11400.

Further, the communication part 11404 receives a control signal for controlling to drive the camera head 11102 from the CCU 11201, and supplies it to the camera head control part 11405. The control signal includes information for designating a frame rate of a shot image, information for designating an exposure value on shooting, and/or information for designating the magnification and the focal point of a shot image and the like, for example.

Additionally, the shooting conditions such as frame rate, exposure value, magnification, and focal point may be designated by the user as needed, or may be automatically set by the control part 11413 in the CCU 11201 on the basis of the obtained image signal. In the latter case, the auto exposure (AE) function, the auto focus (AF) function, and the auto white balance (AWB) function are mounted on the endoscope 11100.

The camera head control part 11405 controls to drive the camera head 11102 on the basis of the control signal from the CCU 11201 received via the communication part 11404.

The communication part 11411 is configured of a communication apparatus for exchanging various items of information with the camera head 11102. The communication part 11411 receives an image signal transmitted from the camera head 11102 via the transmission cable 11400.

Further, the communication part 11411 transmits the control signal for controlling to drive the camera head 11102 to the camera head 11102. The image signal or control signal can be transmitted via electric communication, optical communication, or the like.

The image processing part 11412 performs various image processing on the image signal as RAW data transmitted from the camera head 11102.

The control part 11413 performs various controls for shooting a surgical site or the like by the endoscope 11100 and displaying a shot image obtained by shooting a surgical site or the like. For example, the control part 11413 generates the control signal for controlling to drive the camera head 11102.

Further, the control part 11413 causes the display apparatus 11202 to display a shot image shooting a surgical site or the like therein on the basis of the image signal subjected to the image processing by the image processing part 11412. At this time, the control part 11413 may recognize various objects in the shot image by use of various image recognition technologies. For example, the control part 11413 detects the shapes, colors, and the like of the edges of the objects included in the shot image thereby to recognize a surgical tool such as forceps, a specific living body site, bleeding, mist during the use of the energy treatment tool 11112, and the like. When causing the display apparatus 11202 to display a shot image, the control part 11413 may overlap various items of surgery support information on the image of the surgical site to be displayed by use of the recognition result. The surgery support information is overlapped to be displayed, and is presented to the operator 11131 so that the loads on the operator 11131 can be alleviated and the operator 11131 can securely perform the operation.

The transmission cable 11400 connecting the camera head 11102 and the CCU 11201 is an electric signal cable for communication of electric signals, an optical fiber for optical communication, or a composite cable thereof.

Here, wired communication is made by use of the transmission cable 11400 in the illustrated example, but wireless communication may be made between the camera head 11102 and the CCU 11201.

An exemplary endoscopic surgery system to which the technology according to the present disclosure can be applied has been described above. The technology according to the present disclosure can be applied to the camera head 11102 among the above-described constituents, for example. Specifically, the electronic component 10 in the camera module 1 according to each embodiment described above can be applied to the shooting part 11402. The technology according to the present disclosure is applied to the shooting part 11402 so that the shooting part 11402 can be stably used for a long time.

Additionally, the endoscopic surgery system has been described herein by way of example, but the technology according to the present disclosure may be additionally applied to a microscopic surgery system and the like, for example.

7. Application to Moving Object

Further, the technology according to the present disclosure (the present technology) is applicable to various products. For example, the technology according to the present disclosure may be realized as an apparatus mounted on any kind of moving object such as vehicle, electric vehicle, hybrid vehicle, motorcycle, bicycle, personal mobility, airplane, drone, ship, or robot.

Figure 24:
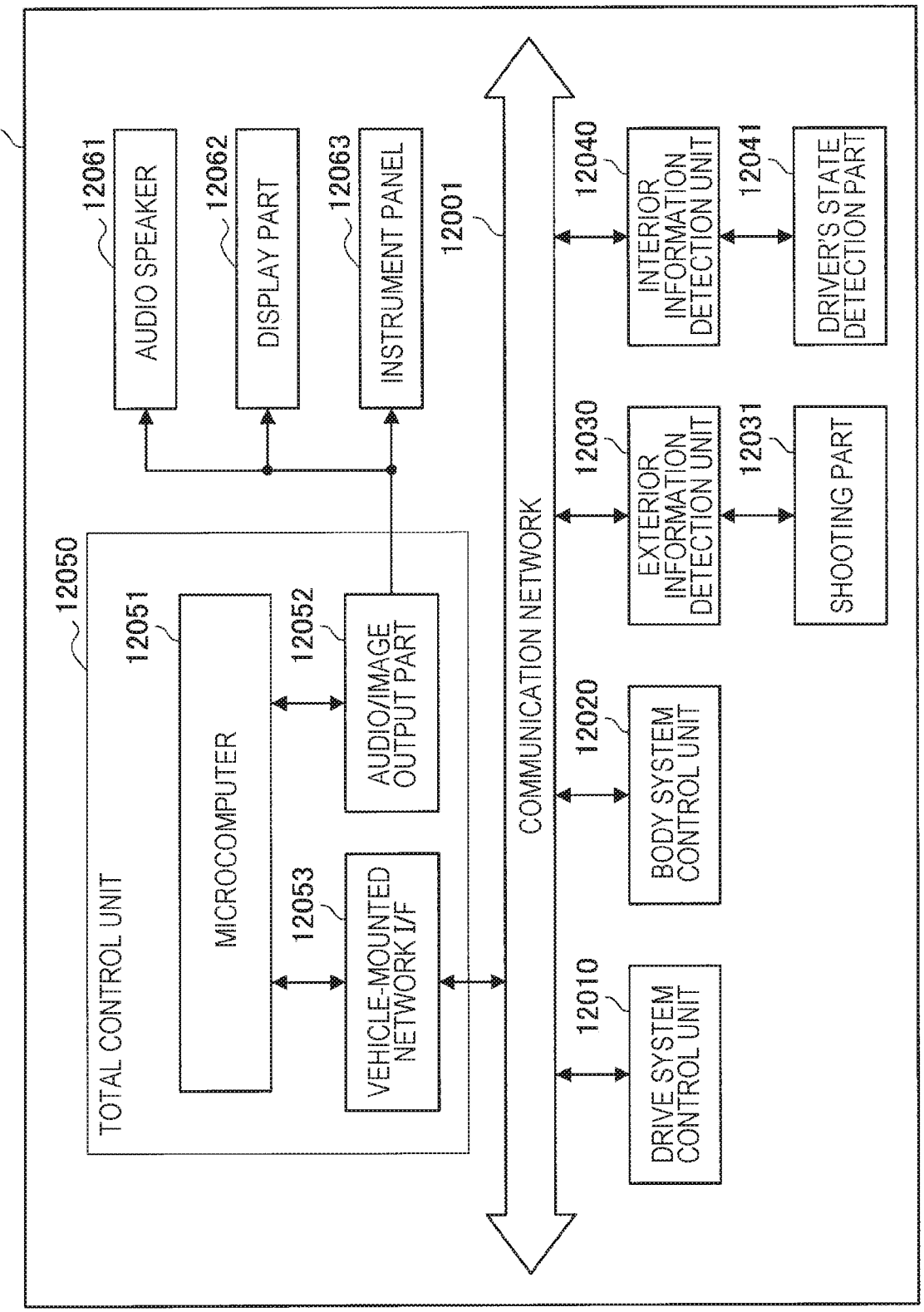
FIG. 24 is a block diagram illustrating an exemplary schematic configuration of a vehicle control system.

FIG. 24 is a block diagram illustrating an exemplary schematic configuration of a vehicle control system as an exemplary moving object control system to which the technology according to the present disclosure can be applied.

A vehicle control system 12000 includes a plurality of electronic control units connected via a communication network 12001. In the example illustrated in FIG. 24, the vehicle control system 12000 includes a drive system control unit 12010, a body system control unit 12020, an exterior information detection unit 12030, an interior information detection unit 12040, and a total control unit 12050. Further, a microcomputer 12051, an audio/image output part 12052, and a vehicle-mounted network interface (I/F) 12053 are illustrated as the functional components of the total control unit 12050.

The drive system control unit 12010 controls the operations of the apparatuses for the vehicle drive system according to various programs. For example, the drive system control unit 12010 functions as a control apparatus for a driving force generation apparatus such as internal engine or drive motor for generating a driving force of the vehicle, a driving force transmission mechanism for transmitting a driving force to the wheels, a steering mechanism for adjusting the steering angle of the vehicle, a braking apparatus for generating a braking force of the vehicle, and the like.

The body system control unit 12020 controls the operations of various apparatuses equipped in the vehicle body according to various programs. For example, the body system control unit 12020 functions as a control apparatus for a keyless entry system, a smart key system, a power window apparatus, or various lights such as head lights, back lights, brake lights, directional signals, or fog lights. In this case, a radio wave originated from a portable machine as a key, or signals of various switches can be input to the body system control unit 12020. The body system control unit 12020 receives the input of the radio wave or signals, and controls the door lock apparatus, the power window apparatus, the lights, and the like of the vehicle.

The exterior information detection unit 12030 detects the information indicating the exterior of the vehicle mounting the vehicle control system 12000 thereon. For example, the exterior information detection unit 12030 is connected with a shooting part 12031. The exterior information detection unit 12030 causes the shooting part 12031 to shoot an image of the exterior of the vehicle, and receives the shot image. The exterior information detection unit 12030 may perform a processing of detecting an object such as person, vehicle, obstacle, road sign, or character on the road, or a distance detection processing on the basis of the received image.

The shooting part 12031 is a light sensor for receiving light and outputting an electric signal depending on the amount of received light. The shooting part 12031 can output the electric signal as an image, or can output it as distance measurement information. Further, light received by the shooting part 12031 may be a visible ray or a non-visible ray such as infrared ray.

The interior information detection unit 12040 detects the information indicating the interior of the vehicle. The interior information detection unit 12040 is connected with a driver's state detection part 12041 for detecting a driver's state, for example. The driver's state detection part 12041 includes a camera for shooting the driver, for example, and the interior information detection unit 12040 may calculate a degree of fatigue or a degree of concentration of the driver or may determine whether the driver is asleep at the wheel on the basis of the detection information input from the driver's state detection part 12041.

The microcomputer 12051 can calculate a control target value of the driving force generation apparatus, the steering mechanism, or the braking apparatus on the basis of the information indicating the exterior or interior of the vehicle obtained by the exterior information detection unit 12030 or the interior information detection unit 12040, and can output a control instruction to the drive system control unit 12010. For example, the microcomputer 12051 can perform cooperative control for realizing the advanced driver assistance system (ADAS) functions including collision avoidance or collision alleviation of the vehicle, follow-up traveling based on inter-vehicle distance, traveling at kept vehicle speed, collision alarm of the vehicle, lane deviation alarm of the vehicle, and the like.

Further, the microcomputer 12051 controls the driving force generation apparatus, the steering mechanism, the braking apparatus, or the like on the basis of the information indicating the surrounding of the vehicle obtained by the exterior information detection unit 12030 or the interior information detection unit 12040, thereby performing cooperative control for automatic driving of autonomous traveling irrespective of driver's operation, and the like.

Further, the microcomputer 12051 can output a control instruction to the body system control unit 12020 on the basis of the information indicating the exterior of the vehicle obtained by the exterior information detection unit 12030. For example, the microcomputer 12051 can control the head lights depending on the position of a leading vehicle or an oncoming vehicle detected by the exterior information detection unit 12030, and can perform cooperative control in order to achieve anti-glare such as switching from high beam to low beam.

The audio/image output part 12052 transmits an output signal of at least one of audio or image to an output apparatus capable of visually or aurally notifying information to the passengers in the vehicle or the outside of the vehicle. In the example of FIG. 24, an audio speaker 12061, a display part 12062, and an instrument panel 12063 are illustrated as output apparatuses by way of example. The display part 12062 may include at least one of an on-board display or a head-up display, for example.

Figure 25:
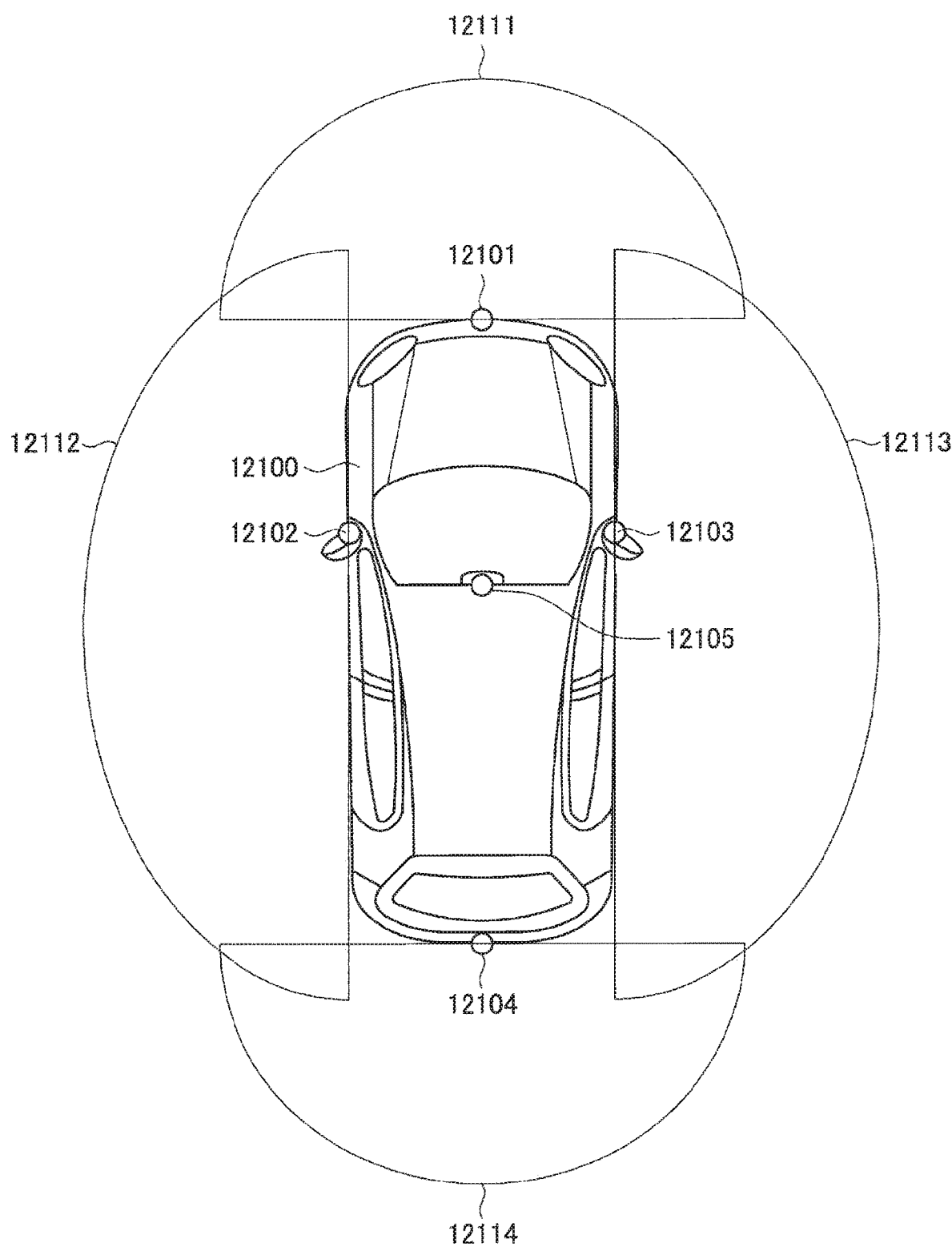
FIG. 25 is an explanatory diagram illustrating exemplary installation positions of an exterior information detection part and shooting parts.

FIG. 25 is a diagram illustrating exemplary installation positions of the shooting part 12031.

In FIG. 25, the vehicle 12100 has the shooting part 12031 including shooting parts 12101, 12102, 12103, 12104, and 12105.

The shooting parts 12101, 12102, 12103, 12104, and 12105 are provided at the front nose, the side mirrors, the rear bumper or back door, at the top part of the front shield inside the vehicle 12100, and the like, for example. The shooting part 12101 provided at the front nose and the shooting part 12105 provided at the top part of the front shield inside the vehicle mainly obtain images in front of the vehicle 12100. The shooting parts 12102 and 12103 provided at the side mirrors mainly obtain images on both sides of the vehicle 12100. The shooting part 12104 provided at the rear bumper or back door mainly obtains an image behind the vehicle 12100. The front images obtained by the shooting parts 12101 and 12105 are mainly used to detect a leading vehicle, a pedestrian, an obstacle, a traffic light, a road sign, a traffic lane, or the like.

Additionally, FIG. 25 illustrates exemplary shooting ranges of the shooting parts 12101 to 12104. A shooting range 12111 indicates a shooting range of the shooting part 12101 provided at the front nose, the shooting ranges 12112 and 12113 indicate the shooting ranges of the shooting parts 12102 and 12103 provided at the side mirrors, respectively, and a shooting range 12114 indicates a shooting range of the shooting part 12104 provided at the rear bumper or back door. For example, the image data shot by the shooting parts 12101 to 12104 are overlapped thereby to obtain a perspective image of the vehicle 12100 viewed from above.

At least one of the shooting parts 12101 to 12104 may have a function of obtaining distance information. For example, at least one of the shooting parts 12101 to 12104 may be a stereo camera configured of a plurality of imaging devices, or may be an imaging device having pixels for phase difference detection.

For example, the microcomputer 12051 finds a distance to each stereoscopic object in the shooting ranges 12111 to 12114 and a temporal change in the distance (relative speed to the vehicle 12100) on the basis of the distance information obtained from the shooting parts 12101 to 12104, thereby extracting, as a leading vehicle, a stereoscopic object traveling at a predetermined speed (0 km/h or more, for example) substantially in the same direction as the vehicle 12100, which is the closest stereoscopic object to the vehicle 12100 on the road. Further, the microcomputer 12051 can set an inter-vehicle distance to be previously secured behind the leading vehicle, and can perform automatic brake control (including follow-up stop control), automatic acceleration control (including follow-up start control), or the like. Cooperative control for automatic driving of autonomous traveling irrespective of driver's operation, and the like can be performed in this way.

For example, the microcomputer 12051 can classify and extract stereoscopic data regarding stereoscopic objects into two-wheel vehicle, standard-sized vehicle, large-sized vehicle, pedestrian, power pole, and the like on the basis of the distance information obtained from the shooting parts 12101 to 12104, and can use it for automatic obstacle avoidance. For example, the microcomputer 12051 discriminates the obstacles around the vehicle 12100 into obstacles capable of being visually confirmed by the driver of the vehicle 12100 and obstacles difficult to visually confirm. The microcomputer 12051 then determines a collision risk indicating a degree of risk of collision with each obstacle, and outputs an alarm to the driver via the audio speaker 12061 or the display part 12062 or performs forcible deceleration or avoidance steering via the drive system control unit 12010 when there is a collision possibility at a set value of collision risk, thereby performing driving support for collision avoidance.

At least one of the shooting parts 12101 to 12104 may be an infrared camera for detecting an infrared ray. For example, the microcomputer 12051 determines whether or not a pedestrian is present in the images shot by the shooting parts 12101 to 12104, thereby recognizing the pedestrian. The pedestrian is recognized in a procedure of extracting the characteristic points in the images shot by the shooting parts 12101 to 12104 as infrared cameras and a procedure of performing a pattern matching processing on a series of characteristic points indicating the contour of an object and determining whether or not the contour of the object is a pedestrian, for example. When the microcomputer 12051 determines that a pedestrian is present in the images shot by the shooting parts 12101 to 12104 and recognizes the pedestrian, the audio/image output part 12052 controls the display part 12062 to overlap a square contour line for emphasis on the recognized pedestrian for display. Further, the audio/image output part 12052 may control the display part 12062 to display an icon or the like indicating a pedestrian at a desired position.

An exemplary vehicle control system to which the technology according to the present disclosure can be applied has been described above. The technology according to the present disclosure can be applied to the shooting part 12031 among the above-described constituents. Specifically, the electronic component 10 in the camera module 1 according to each embodiment described above can be applied to the shooting part 12031. The technology according to the present disclosure is applied to the shooting part 12031 so that the shooting part 12031 can be stably used for a long time irrespective of various travelling environments.

8. Conclusion

The preferred embodiments of the present disclosure have been described above in detail with reference to the accompanying drawings, but the technical scope of the present disclosure is not limited to the examples. It is clear that those skilled in the art in the technical field of the present disclosure can assume various changes or modifications within the scope of the technical spirit described in CLAIMS, and it is of course understood that the changes or modifications belong to the technical scope of the present disclosure.

Further, the effects described in the present specification are merely explanatory or exemplary, and are not restrictive. That is, the technology according to the present disclosure can obtain other effects clear to those skilled in the art from the description of the present specification together with the above effects or instead of the above effects.

Additionally, the following configurations also belong to the technical scope of the present disclosure.

(1)

An electronic component including:

a base material having a main face;

at least one wiring formed on the main face of the base material;

at least one pad provided at each end of the at least one wiring on the main face of the base material;

a resist part formed to cover the at least one wiring on the main face of the base material; and a chip flip-chip mounted on the main face of the base material and connected to the base material via a bump bonded to the at least one pad, in which the resist part has a pad opening configured to expose the at least one pad bonded with the bump, and a circulation groove formed to be connected to the pad opening at one end as a connection end to the pad opening.

(2)

The electronic component according to (1), in which the circulation groove is formed such that the main face of the base material is exposed at the bottom of the circulation groove.

(3)

The electronic component according to (1) or (2), in which the circulation groove is formed in a region other than a region where the at least one wiring is formed on the main face of the base material in plan view.

(4)

The electronic component according to any one of (1) to (3), in which the circulation groove is formed such that an end of the circulation groove opposite to the connection end to the pad opening is positioned outside the chip on the resist part in plan view.

(5)

The electronic component according to (4), in which an end of the circulation groove opposite to the connection end to the pad opening is positioned in a region at a fillet width or less of encapsulation resin sealing between the chip and the base material from a peripheral end of the chip.

(6)

The electronic component according to any one of (1) to (5), in which a plurality of the pads is arranged in a line on the main face of the base material, and the pad opening is formed in a groove shape to transversely expose a plurality of the pads.

(7)

The electronic component according to any one of (1) to (5), in which a plurality of the pads is arranged in a plurality of lines on the main face of the base material, and the pad opening is formed in a groove shape to transversely expose a plurality of the pads.

(8)

The electronic component according to (6) or (7), in which the circulation groove includes a circulation groove formed to extend in a direction orthogonal to a direction in which the groove-shaped pad opening is formed.

(9)

The electronic component according to any one of (6) to (8), in which the circulation groove includes a circulation groove connected to an end of the groove-shaped pad opening at the connection end of the circulation groove.

(10)

The electronic component according to any one of (1) to (9), in which a groove width of the circulation groove at the connection end of the circulation groove to the pad opening is larger than a groove width of the circulation groove at a part other than the connection end of the circulation groove.

(11)

The electronic component according to any one of (1) to (10), further including:

a translucent member which opposes an opposite face of the main face of the base material and has optical transparency, in which the chip includes an imaging device having a light receiving face on a side opposing the translucent member, and the base material and the resist part have main openings where a region corresponding to the light receiving face is opened in plan view, respectively.

(12)

The electronic component according to (11), further including:

a dam part formed along an opening peripheral end of a main opening of the resist part and protruded from a surface of the resist part at least in side view.

(13)

The electronic component according to (12), in which the dam part is provided to cover an opening peripheral end of a main opening of the base material.

(14)

The electronic component according to (12) or (13), in which the dam part is made of absorbent resin.

(15)

The electronic component according to any one of (11) to (14), in which the resist part further includes a groove-shaped first trap part formed in a direction along an opening peripheral end of a main opening of the resist part.

(16)

The electronic component according to any one of (1) to (15), in which the resist part further includes a groove-shaped second trap part formed in a direction along a boundary of a region inside the region corresponding to the chip in plan view.

(17)

The electronic component according to any one of (1) to (16), further including:

encapsulation resin provided between a circuit board including the base material, the at least one wiring, and the resist part, and the chip, and sealing between the circuit board and the chip and fixing the circuit board and the chip, in which the encapsulation resin covers an entire side peripheral face of the bump.

(18)

A camera module including:

a base material having a first face and a second face opposite to the first face;

at least one wiring formed on the first face of the base material;

at least one pad provided at each end of the at least one wiring on the first face of the base material;

a resist part formed to cover the at least one wiring on the first face of the base material;

a translucent member provided to oppose the second face of the base material and having optical transparency;

an imaging device flip-chip mounted on the first face of the base material, having a light receiving face on a side opposing the translucent member, and connected to the base material via a bump bonded to the at least one pad; and a lens unit provided opposite to a side of the translucent member opposing the base material, in which the base material and the resist part have main openings where a region corresponding to the light receiving face is opened in plan view, respectively, and the resist part has a pad opening configured to expose the at least one pad bonded with the bump, and a circulation groove formed to connect to the pad opening at one end as a connection end to the pad opening.

REFERENCE SIGNS LIST

1 Camera module
2 Lens unit
3 Group of lenses
4 Holder
5 Housing
10 Electronic component
11 Circuit board
11B Main opening
12 Imaging device
13 Translucent member
14 Bump
15 Encapsulation resin
16 Passive component
17 Reinforcement plate 30, 35 Dam part
31, 31A Trap part (first trap part)
32 Trap part (second trap part)
111 Base material
111A Main face
112 Wiring
113 Resist part
113A, 113B Pad opening
120, 121 Pad
125 Light receiving face
130, 131, 132, 133 Circulation groove

The invention claimed is:

1. An electronic component, comprising:
a base material having a main face;
at least one wiring on the main face of the base material;
at least one pad at one end of the at least one wiring;
a resist part that covers the at least one wiring; and
a chip flip-chip mounted on the main face of the base material, wherein
the chip is connected to the base material via a bump bonded to the at least one pad, and
the resist part has:
a pad opening configured to expose the at least one pad bonded with the bump; and
a circulation groove connected to one end of the pad opening as a connection end to the pad opening, wherein the main face of the base material is exposed at a bottom side of the circulation groove.

2. The electronic component according to claim 1, wherein
the at least one wiring is in a first region of the main face of the base material,
the circulation groove is in a second region of the main face of the base material, and
the first region is different from the second region.

3. The electronic component according to claim 1, wherein an end of the circulation groove opposite to the connection end to the pad opening is outside the chip on the resist part.

4. The electronic component according to claim 1, further comprising a plurality of pads in a line on the main face of the base material, wherein
the plurality of pads includes the at least one pad, and
the pad opening has a groove shape that transversely exposes the plurality of pads.

5. The electronic component according to claim 4, wherein the circulation groove extends in a direction orthogonal to a direction of the pad opening.

6. The electronic component according to claim 1, further comprising a plurality of pads in a plurality of lines on the main face of the base material, wherein
the plurality of pads includes the at least one pad, and
the pad opening has a groove shape that transversely exposes the plurality of pads.

7. The electronic component according to claim 1, wherein a first groove width of the circulation groove at the connection end to the pad opening is larger than a second groove width of the circulation groove at a part other than the connection end to the pad opening.

8. The electronic component according to claim 1, further comprising:
a translucent member which opposes an opposite face of the main face of the base material, wherein
the translucent member is optically transparent,
the chip includes an imaging device having a light receiving face on a side opposite to the translucent member,
the base material has a first main opening, and
the resist part has a second main opening.

9. The electronic component according to claim 8, further comprising:
a dam part along an opening peripheral end of the second main opening of the resist part,
wherein the dam part protrudes from an upper surface of the resist part.

10. The electronic component according to claim 9, wherein the dam part covers an opening peripheral end of the first main opening of the base material.

11. The electronic component according to claim 9, wherein the dam part is made of absorbent resin.

12. The electronic component according to claim 1, wherein
the resist part further comprises a groove-shaped trap part in a direction along an opening peripheral end of a main opening of the resist part, and
the groove-shaped trap part is configured to control flow of encapsulation resin in the electronic component.

13. The electronic component according to claim 1, wherein
the resist part further comprises a groove-shaped trap part in a direction along a boundary of a region corresponding to the chip, and
the groove-shaped trap part is configured to control a filling process of encapsulation resin in the electronic component.

14. The electronic component according to claim 1, further comprising:
encapsulation resin between a circuit board and the chip, wherein
the circuit board includes the base material, the at least one wiring, and the resist part, and
the encapsulation resin covers an entire side peripheral face of the bump.

15. A camera module, comprising:
a base material having a first face and a second face opposite to the first face;
at least one wiring on the first face of the base material;
at least one pad at one end of the at least one wiring;
a resist part that covers the at least one wiring;
a translucent member opposite to the second face of the base material, wherein the translucent member is optically transparent;
an imaging device flip-chip mounted on the first face of the base material, wherein
the imaging device has a light receiving face on a side opposite to the translucent member, and
the imaging device is connected to the base material via a bump bonded to the at least one pad; and
a lens unit opposite to a side of the translucent member that opposes the base material, wherein
the light receiving face is configured to receive light from the lens unit, and
the resist part has:
a pad opening configured to expose the at least one pad bonded with the bump; and
a circulation groove connected to one end of the pad opening as a connection end to the pad opening, wherein the first face of the base material is exposed at a bottom side of the circulation groove.

* * * * *